United States Patent
Nishikaze et al.

(10) Patent No.: US 12,216,113 B2
(45) Date of Patent: Feb. 4, 2025

(54) METHOD FOR PREPARING ANALYSIS SAMPLE, ANALYSIS METHOD, AND KIT FOR PREPARING ANALYSIS SAMPLE

(71) Applicant: SHIMADZU CORPORATION, Kyoto (JP)

(72) Inventors: Takashi Nishikaze, Kyoto (JP); Hisatoshi Hanamatsu, Sapporo (JP); Jun-ichi Furukawa, Sapporo (JP); Ikuko Yokota, Sapporo (JP)

(73) Assignee: SHIMADZU CORPORATION, Kyoto (JP)

( * ) Notice: Subject to any disclaimer, the term of this patent is extended or adjusted under 35 U.S.C. 154(b) by 539 days.

(21) Appl. No.: 17/073,608

(22) Filed: Oct. 19, 2020

(65) Prior Publication Data

US 2021/0164989 A1 Jun. 3, 2021

(30) Foreign Application Priority Data

Oct. 21, 2019 (JP) ................. 2019-192037

(51) Int. Cl.
*G01N 33/50* (2006.01)
*C07H 1/00* (2006.01)

(52) U.S. Cl.
CPC ........... *G01N 33/50* (2013.01); *C07H 1/00* (2013.01); *G01N 2400/00* (2013.01); *G01N 2560/00* (2013.01)

(58) Field of Classification Search
None
See application file for complete search history.

(56) References Cited

U.S. PATENT DOCUMENTS

2009/0311793 A1  12/2009  Nishimura et al.
2018/0059094 A1   3/2018  Nishikaze

FOREIGN PATENT DOCUMENTS

| CN | 107430113 A | * | 12/2017 | ............... C07H 1/00 |
|---|---|---|---|---|
| JP | 4899067 B2 | | 3/2012 | |
| JP | 2013-076629 A | | 4/2013 | |
| JP | 6135710 B2 | | 5/2017 | |
| WO | 2015/075139 A | | 5/2015 | |

OTHER PUBLICATIONS

Sigma-Aldrich, Safety Data Sheet of Ammonium hydroxide solution 221228, 2021, Sigma-Aldrich (Year: 2021).*

(Continued)

*Primary Examiner* — Paul S Hyun
*Assistant Examiner* — Mickey Huang
(74) *Attorney, Agent, or Firm* — Sughrue Mion, PLLC

(57) ABSTRACT

A method for preparing an analysis sample from a sample containing a glycan, includes: performing esterification reaction that subjects at least a part of a sialic acid included in the glycan to esterification other than lactonization; and performing amidation reaction that converts an esterified form of a sialic acid modified through the esterification into an amidated form through contacting the sample with an amidation reaction solution containing at least one compound selected from the group consisting of ammonia, amines, hydrazine, hydrazine derivatives, and hydroxyamine, and salts thereof to be reacted with the sialic acid modified through the esterification.

24 Claims, 20 Drawing Sheets

(56) References Cited

OTHER PUBLICATIONS

Lageveen-Kammeijer et al., Highly sensitive CE-ESI-MS analysis of N-glycans from complex biological samples, May 2019, Nature Communications, 10: 2137 (Year: 2019).*

The Extended European Search Report dated Mar. 16, 2021, issued by the European Patent Office in application No. 20202649.8.

Yang et al., "Solid-Phase Chemical Modification for Sialic Acid Linkage Analysis: Application to Glycoproteins of Host Cells Used in Influenza Virus Propagation", Anal. Chem., 2017, vol. 89, pp. 9508-9517 (10 pages).

Furukawa et al., "Lactone-Driven Ester-to-Amide Derivatization for Sialic Acid Linkage-Specific Alkylamidation", Anal. Chem., 2020, vol. 92, pp. 14383-14392 (10 pages).

Takashi Nishikaze et al., "Differentiation of Sialyl Linkage Isomers by One-Pot Sialic Acid Derivatization for Mass Spectrometry-Based Glycan Profiling", Analytical Chemistry, (U.S.A.), ACS Publications, Feb. 21, 2017, pp. 2353-2360, vol. 89, Issue 4.

Hisatoshi Hanamatsu et al., "Sialic Acid Linkage Specific Derivatization of Glycosphingolipid Glycans by Ring-Opening Aminolysis of Lactones", Analytical Chemistry, (U.S.A.), ACS Publications, Oct. 29, 2018, pp. 13193-13199, vol. 90, Issue 22.

Susan F. Wheeler et al., "Derivatization of sialic acids for stabilization in matrix-assisted laser desorption/ionization mass spectrometry and concomitant differentiation of a(2→3)- and a(2→6)-isomers", Rapid Communications in Mass Spectrometry, (U.K.), John Wiley and Sons Ltd., Jan. 2009, pp. 303-312, vol. 23, Issue 2.

Karli R. Reiding et al., "High-Throughput Profiling of Protein N-Glycosylation by MALDITOF-MS Employing Linkage-Specific Sialic Acid Esterification", Analytical Chemistry, (U.S.A.), ACS Publications, Jun. 2014, pp. 5784-5793, vol. 86, Issue 12.

Henghui Li et al., "MALDI-MS analysis of sialylated N-glycan linkage isomers using solidphase two step derivatization method", Analytica Chimica Acta, (The Netherlands), Elsevier B.V., Jun. 14, 2016, pp. 77-85, vol. 924.

Shuang Yang et al., "Identification of Sialic Acid Linkages on Intact Glycopeptides via Differential ChemicalModification Using IntactGIG-HILIC", Journal of the American Society for Mass Spectrometry., (U.S.A.), Springer, Apr. 12, 2018, pp. 1273-1283, vol. 29, Issue 6.

Guinevere S.M. Lageveen-Kammeijer et al., "Highly sensitive CE-ESI-MS analysis of N-glycans from complex biological samples", Nature Communications, (U.K.), Nature Pub. Group, May 13, 2019, vol. 10, Issue 1, p. 2137.

Takashi Nishikaze et al., "A universal approach to linkage-specific derivatization for sialic acids on glycopeptides", Journal of the American Society for Mass Spectrometry, Jun. 2017, 1page, vol. 28, Issue 1 Supplement, No. MP091.

William R. Alley, Jr. et al., "Glycomic Analysis of Sialic Acid Linkages in Glycans Derived from Blood Serum Glycoproteins", American Chemical Society, Journal of Proteome Research 2010, pp. 3062-3072, vol. 9, No. 6.

Stephanie Holst et al., "Linkage-Specific in Situ Sialic Acid Derivatization for N-Glycan Mass Spectrometry Imaging of Formalin-Fixed Paraffin-Embedded Tissues", Analytical Chemistry 2016, 88, pp. 5904-5913.

Yohei Ishibashi et al., "A Novel Endoglycoceramidase Hydrolyzes Oligogalactosylceramides to Produce Galactooligosaccharides and Ceramides", Journal of Biological Chemistry, Apr. 13, 2007, pp. 11386-11396, vol. 282, No. 15.

Office Action dated Jan. 10, 2023 from the Japanese Patent Office in Application No. 2019-192037.

Communication dated Mar. 1, 2023, issued in European Application No. 20 202 649.8.

Shuang Yang et al., "Supplementary Information for: Solid-phase chemical modification for sialic acid linkage analysis: Application to glycoproteins of host cells used in influenza virus propagation", Analytical Chemistry, 2017, pp. S1-S23 (23 pages).

Noriko Suzuki et al., "Quantitative LC-MS and MS/MS analysis of sialylated glycans modified by linkage-specific alkylamidation", Analytical Biochemistry, 2019, vol. 567, pp. 117-127 (11 pages).

Takashi Nishikaze, "Sialic acid derivatization for glycan analysis by mass spectrometry", Proc. Jpn. Acad., Ser. B, 2019, vol. 95, No. 9, pp. 523-537 (15 pages).

Japanese Office Action dated Sep. 5, 2023 in Japanese Application No. 2019-192037.

Chinese Office Action issued Feb. 23, 2024 in Application No. 202011132543.0.

Communication dated Jul. 2, 2024 issued by the European Patent Office in application No. 20202649.8.

Tamas Pongracz, et al., "The structure and role of lactone intermediates in linkage-specific sialic acid derivatization reactions", Glycoconjugate Journal, 2021, vol. 38, No. 2, pp. 157-166.

Chinese Office Action dated Oct. 11, 2024 in Application No. 202011132543.0.

* cited by examiner

GD1a

GD1b

A2GN1

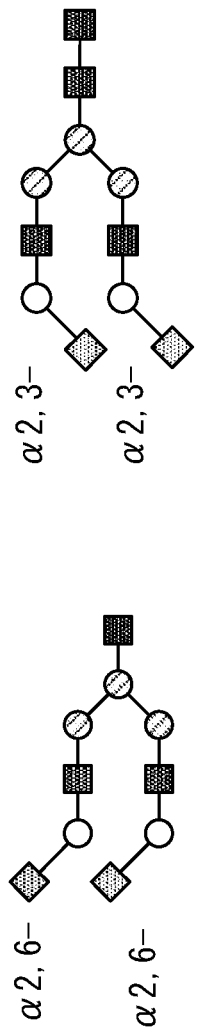
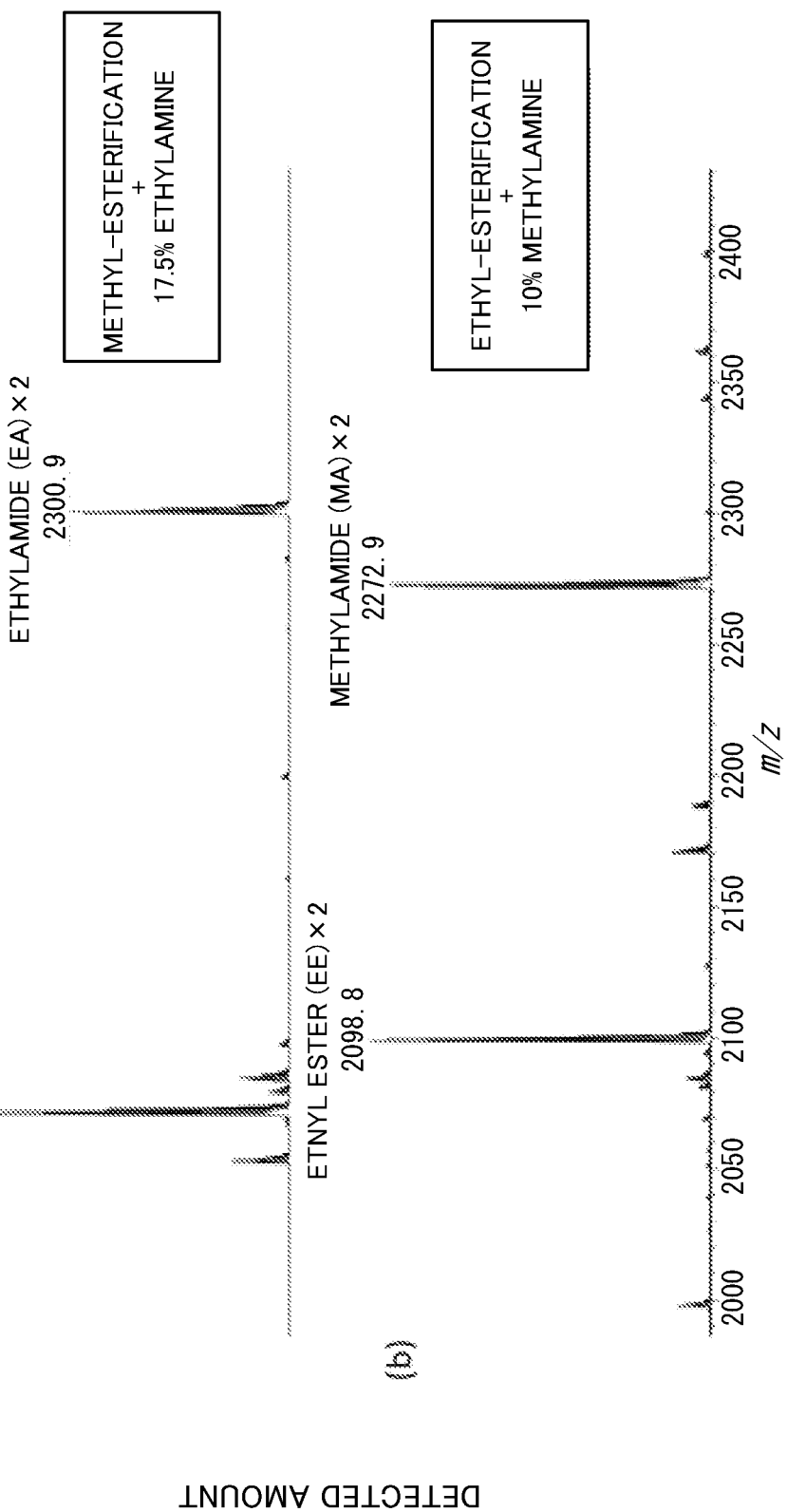
FIG. 10

METHOD FOR PREPARING ANALYSIS SAMPLE, ANALYSIS METHOD, AND KIT FOR PREPARING ANALYSIS SAMPLE

INCORPORATION BY REFERENCE

The disclosures of the following priority application and the following publications are herein incorporated by reference:

Japanese Patent Application No. 2019-192037 filed Oct. 21, 2019

Takashi Nishikaze, Sadanori Sekiya, Shinichi Iwamoto, Koichi Tanaka. "A Universal Approach to linkage-Specific Derivatization for Sialic Acids on Glycopeptides," Journal of The American Society for Mass Spectrometry, June, 2017, Volume 28, Issue 1 Supplement, Poster No. MP091.

Ishibashi Y, Nakasone T, Kiyohara M, Horibata Y, Sakaguchi K, Hijikata A, Ichinose S, Omori A, Yasui Y, Imamura A, Ishida H, Kiso M, Okino N, and I to M. "A novel endoglycoceramidase hydrolyzes oligogalactosylceramides to produce galactooligosaccharides and ceramides," Journal of Biological Chemistry, 2007, Volume 282, pp. 11386-11396

TECHNICAL FIELD

The present invention relates to a method for preparing an analysis sample, an analysis method, and a kit for preparing an analysis sample.

BACKGROUND ART

Sialic acid is a saccharide abundant in a living body. Sialic acid is included in glycans linked to protein in the living body, and is often present at a non-reducing end of a glycan. Thus, sialic acid is positioned in the outermost side of such a glycoprotein molecule, and plays an important role because it is directly recognized by other molecules.

Sialic acids may have different linkage types to the adjacent saccharide. For example, $\alpha 2,3$- and $\alpha 2,6$-linkage types are primarily known for human N-linked glycans (N-glycans), and in addition to these linkage types, $\alpha 2,8$- and $\alpha 2,9$-linkage types are known for O-linked glycans (O-glycans) and glycosphingolipids. Sialic acids with such different linkage types are recognized by different molecules, and thus can play different roles.

In mass spectrometry or the like, glycans including sialic acid is subjected to modification of sialic acid as pretreatment. This neutralizes the negatively charged carboxy group of sialic acid through esterification, amidation, or the like, to overcome disadvantages such as suppression of ionization and loss of sialic acid. In the case of lactonization of sialic acid, the stability of a lactone to be formed varies among linkage types, and hence utilization of the difference in stability enables linkage-specific modification and analysis of sialic acids.

However, lactones are extremely unstable, easily hydrolyzed even in water, and more quickly hydrolyzed under acidic or basic conditions. For this reason, stabilization of lactones formed through modification in pretreatment by amidation has been reported (see PTL 1, NPTL 1, and NPTL 2). A cyclic structure in a molecule generated through lactonization is appropriately called a lactone structure. Lactone structures are present, for example, in glycans in the living body and even in glycans in antibody drugs, and stabilization can be similarly performed when analyzing them. Direct amidation of lactones described in NPTL 2 enables quick modification of lactones, and is expected to be widely used in the future.

Lactonization is one mode of esterification. Esterification other than lactonization is currently used for modification of sialic acid. In NPTL 3, a dehydration condensation agent 4-(4,6-dimethoxy-1,3,5-triazin-2-yl)-4-methylmorpholinium chloride (DMT-MM) is added to a free glycan dissolved in methanol. Thereby, $\alpha 2,6$-sialic acid is methyl-esterified and $\alpha 2,3$-sialic acid is lactonized.

In NPTL 4, dehydration condensation agents such as N-(3-dimethylaminopropyl)-N'-ethylcarbodiimide (EDC) and 1-hydroxybenzotriazole (HOBt) dissolved in ethanol or the like are added to a free glycan. Thereby, $\alpha 2,6$-sialic acid is esterified and $\alpha 2,3$-sialic acid is lactonized.

In NPTL 5, a solution containing ethanol and dehydration condensation agents is added to glycoproteins bonded to a solid phase carrier, thereby esterifying $\alpha 2,6$-sialic acid and lactonizing $\alpha 2,3$-sialic acid. Thereafter, Tris buffer at pH 10 is added to the sample for hydrolysis of lactones, as illustrated in Scheme 1(b) in NPTL 5, the sample is reacted for 1 hour, and a solution containing methylamine hydrochloride is then added to the sample, to which a dehydration condensation agent is further added and the resultant is reacted for 30 minutes.

In NPTL 6, ethanol containing EDC hydrochloride and HOBt is added to glycoproteins bonded to a solid phase carrier to esterify $\alpha 2,6$-sialic acid, and p-toluidine solution together with a dehydration condensation agent is then added to the sample to amidate $\alpha 2,3$-sialic acid.

In NPTL 7, ethanol containing EDC hydrochloride and HOBt is added to a glycoprotein bonded to a solid phase carrier to esterify $\alpha 2,6$-sialic acid, and ethylenediamine solution together with a dehydration condensation agent is then added to the sample to amidate $\alpha 2,3$-sialic acid.

In NPTL 8, ethanol containing EDC and HOBt is added to glycans to esterify $\alpha 2,6$-sialic acid and lactonize $\alpha 2,3$-sialic acid, and ammonia water is then added thereto and the resultant is reacted in the presence of the dehydration condensation agents to hydrolyze lactones and then amidate.

CITATION LIST

Patent Literature

PTL 1: Japanese Patent No. 6135710

Non-Patent Literature

NPTL 1: Nishikaze T, Tsumoto H, Sekiya S, Iwamoto S, Miura Y, Tanaka K. "Differentiation of Sialyl Linkage Isomers by One-Pot Sialic Acid Derivatization for Mass Spectrometry-Based Glycan Profiling" Analytical Chemistry, (U.S.A.), ACS Publications, Feb. 21, 2017, Volume 89, Issue 4, pp. 2353-2360

NPTL 2: Hanamatsu H, Nishikaze T, Miura N, Piao J, Okada K, Sekiya S, Iwamoto S, Sakamoto N, Tanaka K, Furukawa J I. "Sialic Acid Linkage Specific Derivatization of Glycosphingolipid Glycans by Ring-Opening Aminolysis of Lactones" Analytical Chemistry, (U.S.A.), ACS Publications, Oct. 29, 2018, Volume 90, Issue 22, pp. 13193-13199

NPTL 3: Wheeler S F, Domann P, Harvey D J. "Derivatization of sialic acids for stabilization in matrix-assisted laser desorption/ionization mass spectrometry and concomitant differentiation of alpha(2→3)- and alpha(2→6)- isomers" Rapid communications in mass spectrometry, (U.K.), John Wiley And Sons Ltd., January, 2009, Volume 23, Issue 2, pp. 303-12

NPTL 4: Reiding K R, Blank D, Kuijper D M, Deelder A M, Wuhrer M. "High-throughput profiling of protein N-glycosylation by MALDI-TOF-M S employing linkage-specific sialic acid esterification" Analytical Chemistry, (U.S.A.), ACS Publications, June, 2014, Volume 86, Issue 12, pp. 5784-93

NPTL 5: Li H, Gao W, Feng X, Liu B F, Liu X. "MALDI-M S analysis of sialylated N-glycan linkage isomers using solid-phase two step derivatization method," Analytica Chimica Acta, (the Netherlands), Elsevier B. V., Jun. 14, 2016, Volume 924, pp. 77-85

NPTL 6: Yang S, Jankowska E, Kosikova M, Xie H, Cipollo J. "Solid-Phase Chemical Modification for Sialic Acid Linkage Analysis: Application to Glycoproteins of Host Cells Used in Influenza Virus Propagation" Analytical Chemistry, (U.S.A.), ACS Publications, September, 2017, Volume 89, Issue 17, pp. 9508-17

NPTL 7: Yang S, Wu W W, Shen R F, Bern M, Cipollo J "Identification of Sialic Acid Linkages on Intact Glycopeptides via Differential Chemical Modification Using IntactGIG-HILIC" Journal of the American Society for Mass Spectrometry., (U.S.A.), Springer, Apr. 12, 2018, Volume 29, Issue 6, pp. 1273-1283

NPTL 8: Lageveen-Kammeijer G S M, de Haan N, Mohaupt P, Wagt S, Filius M, Nouta J, Falck D, Wuhrer M. "Highly sensitive CE-ESI-MS analysis of N-glycans from complex biological samples" Nature communications, (U.K.), Nature Pub. Group, May 13, 2019, Volume 10, Issue 1, p. 2137

SUMMARY OF INVENTION

Technical Problem

It is desired for analysis of a sialic acid included in a glycan that a novel method for modifying a sialic acid included in a glycan be proposed.

Solution to Problem

The 1st aspect of the present invention relates to a method for preparing an analysis sample from a sample containing a glycan, the method comprising: performing esterification reaction that subjects at least a part of a sialic acid included in the glycan to esterification other than lactonization; and performing amidation reaction that converts an esterified form of a sialic acid modified through the esterification into an amidated form through contacting the sample with an amidation reaction solution containing at least one compound selected from the group consisting of ammonia, amines, hydrazine, hydrazine derivatives, and hydroxyamine, and salts thereof to be reacted with the sialic acid modified through the esterification.

The 2nd aspect of the present invention relates to an analysis method comprising: preparing a sample by using the method for preparing an analysis sample according to the 1st aspect; and performing analysis of the analysis sample prepared.

The 3rd aspect of the present invention relates to a kit for preparing an analysis sample, wherein the kit is used for the method for preparing an analysis sample according to the 1st aspect.

Advantageous Effects of Invention

The present invention can provide a method for modifying a sialic acid with use of a novel mechanism for analysis of a sialic acid included in a glycan.

BRIEF DESCRIPTION OF DRAWINGS

FIG. 4A shows a conceptual diagram illustrating the structure of the glycan GD1a.

FIG. 10 shows (a) a mass spectrum of an analysis sample prepared in such a manner that methyl-esterification reaction was performed and amidation reaction was then performed by using 17.5% ethylamine solution, and (b) a mass spectrum of an analysis sample prepared in such a manner that ethyl-esterification reaction was performed and amidation reaction was then performed by using 10% methylamine solution.

DESCRIPTION OF EMBODIMENTS

Hereinafter, embodiments of the present invention will be described with reference to the drawings. In the embodiments below, the term "esterification" refers to esterification other than lactonization, unless otherwise noted.

First Embodiment

Figure 1:
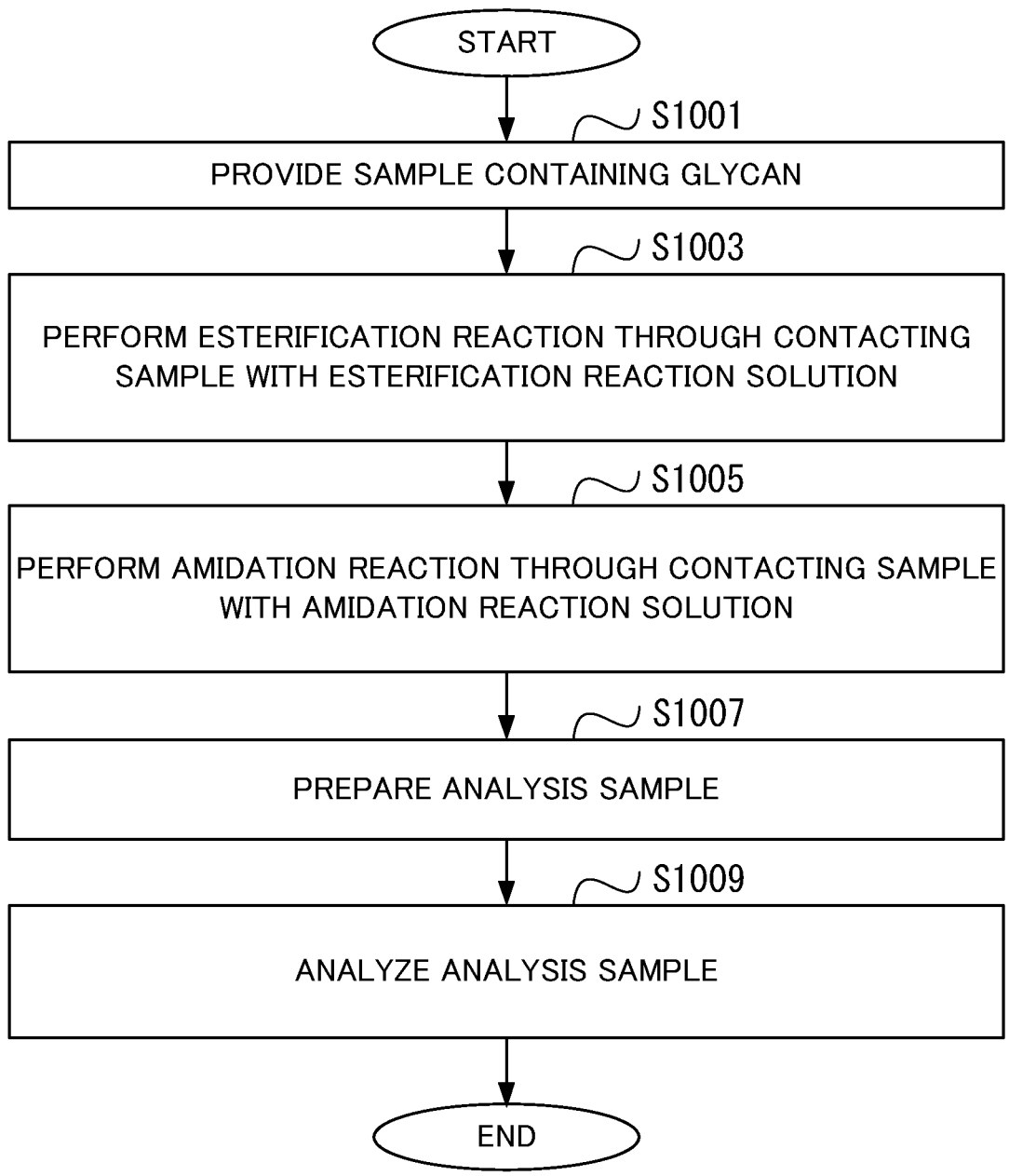
FIG. 1 shows a flowchart illustrating the procedure of an analysis method according to one embodiment.

FIG. 1 shows a flowchart illustrating the procedure of an analysis method according to a method for preparing an analysis sample (sample for analysis) in the present embodiment. In the method for preparing an analysis sample in the present embodiment, sialic acids included in a glycan contained in a sample are esterified, and esterified sialic acids are then amidated in a linkage-specific manner. A sample containing a glycan is prepared in step S1001.

Sample

The sample containing a glycan is not limited, and can contain at least one molecule selected from the group consisting of a glycan, a glycopeptide and a glycoprotein, and a glycolipid. A peptide and a glycopeptide can include a peptide main chain consisting of 2 or more and less than 50 amino acids, and a protein and a glycoprotein can include a peptide main chain consisting of 50 or more amino acids. However, there exist conventional exceptions, and the classification boundary between a peptide and a protein and that between a glycopeptide and a glycoprotein are not limited to those mentioned. In the method for preparing an analysis sample in the present embodiment, linkage-specific modification is performed for a sialic acid included in a glycan. It is preferable for the glycan in the sample to contain a glycan which may have a sialic acid at an end or a position other than ends such as a N-linked glycan (N-glycan), an O-linked glycan (O-glycan), and a glycolipid-type glycan. It is more preferable that the glycan in the sample include or may include at least one of α2,3-sialic acid, α2,8-sialic acid, and α2,9-sialic acid, and it is even more preferable that the glycan in the sample include or may include α2,6-sialic acid, additionally.

If a sample containing a free glycan is used, the glycan can be a glycan released from a glycoprotein, a glycopeptide, or a glycolipid. For the release method, for example, enzymatic treatment using N-glycosidase, 0-glycosidase, or endoglycoceramidase, or hydrazinolysis, β-elimination by alkali treatment, or the like may be used. In releasing a N-linked glycan from the peptide chain of glycopeptide or glycoprotein, enzyme treatment is suitably used, for example, with peptide-N-glycosidase F (PNGase F), peptide-N-glycosidase A (PNGase A), or endo-β-N-acetylglucosaminidase (Endo M). Alternatively, modification such as pyridylamination (PA labeling) can be appropriately performed for the reducing end of the glycan. Cleavage of the peptide chain of a glycopeptide or a glycoprotein, which is described later, may be performed before the enzyme treatment.

When the sample contains a glycopeptide or a glycoprotein, treatment to suppress side reaction of the peptide moiety can be appropriately performed, as described later in the section "Suppression of Side Reaction of Glycopeptide and Glycoprotein". In the case that the peptide chain of the glycopeptide or glycoprotein includes a large number of amino acid residues, it is preferable to cleave the peptide chain, for example, through enzymatic cleavage. In preparing a sample for mass spectrometry, for example, the number of amino acid residues in the peptide chain is preferably 30 or less, more preferably 20 or less, and even more preferably 15 or less. In the case that the origin of peptide to which a glycan is linked is needed to be clarified, the number of amino acid residues in the peptide chain is preferably two or more, and more preferably three or more.

A digestive enzyme is used in cleaving the peptide chain of a glycopeptide or a glycoprotein, and examples thereof include trypsin, lysyl endopeptidase, arginine endopeptidase, chymotrypsin, pepsin, thermolysin, proteinase K, and pronase E. Two or more of these digestive enzymes may be used in combination. Conditions for cleavage of the peptide chain are not limited, and a protocol suitable for the digestive enzyme to be used is appropriately employed. Before the cleavage, denaturation treatment or alkylation treatment may be performed for the protein or peptide in the sample. Conditions for the denaturation treatment or alkylation treatment are not limited. The cleavage of the peptide chain may be achieved not through enzymatic cleavage but through chemical cleavage or any other method.

The completion of step S1001 is followed by step S1003.

Esterification Reaction

In step S1003, esterification reaction is performed (hereinafter, the expression "esterification reaction" refers to the esterification reaction in step S1003, unless otherwise stated) that esterifies at least a part of sialic acids included in the glycan through contacting the sample with a reaction solution for esterification (hereinafter, referred to as "esterification reaction solution"). The esterification reaction is a reaction that subjects a sialic acid included in the glycan to esterification other than lactonization. If a part of sialic acids undergoes esterification other than lactonization in the esterification reaction, however, other parts of sialic acids may be laconized. In the present and subsequent embodiments, "esterification other than lactonization" refers to the phenomenon that some of the components of the esterification reaction solution bond to the carboxylic acid of sialic acid to form carboxylate ester. This means that some of the components of the esterification reaction solution are introduced into the moiety R in —COOR, which represents carboxylate ester. It is preferable that sialic acids included in the glycan be esterified in a manner nonspecific to linkage type in the esterification reaction. In the esterification reaction, carboxy groups of α2,3-sialic acid, α2,6-sialic acid, α2,8-sialic acid, and α2,9-sialic acid are suitably esterified.

The composition of the esterification reaction solution is not limited, and may be any composition that can esterify at least a part of sialic acids included in the glycan, in particular, at least a sialic acid other than α2,6-sialic acid, such as α2,3-sialic acid. For linkage-specific modification, it is preferable that α2,6-sialic acid be also esterified. It is preferable that the esterification reaction solution contain at least one of an alcohol and an esterifying agent. There is no limitation to the esterification method using an alcohol or an esterifying agent, and any esterification method can be used.

Esterification Reaction Solution Containing Alcohol

If the esterification reaction solution contains an alcohol, it is preferable that the esterification reaction solution further contain a condensing agent, and it is more preferable that the esterification reaction solution contain an additive in addition to a condensing agent. The esterification reaction solution may be configured to contain an alcohol such as methanol and ethanol and an acid such as hydrochloric acid.

The alcohol contained in the esterification reaction solution is not limited, and may be an alcohol of any hydroxy group number. The alcohol contained in the esterification reaction solution is preferably a monohydric alcohol, more preferably methanol, ethanol, propanol, butanol, pentanol, or hexanol, and even more preferably methanol or ethanol.

The condensing agent contained in the esterification reaction solution is not limited. At least one of carbodiimides, carbodiimidazoles, phosgene derivatives, phosphonium-based condensing agents, uronium-based condensing agents, formamidinium-based condensing agents, and triflate reagents may be contained as the condensing agent.

Examples of carbodiimides as the condensing agent include 1-cyclohexyl-3-(2-morpholinoethyl)carbodiimide metho-p-toluenesulfonate (CMC), 1-(3-dimethylaminopropyl)-3-ethylcarbodiimide (EDAC), N,N'-dicyclohexylcarbodiimide (DCC), N-(3-dimethylaminopropyl)-N'-ethylcarbodiimide (EDC), N,N'-diisopropylcarbodiimide (DIC), 1-tert-butyl-3-ethylcarbodiimide (BEC), N,N'-di-tert-butylcarbodiimide, 1,3-di-p-toluylcarbodiimide, bis(2,6-diisopropylphenyl)carbodiimide, bis(trimethylsilyl)carbodiimide, and 1,3-bis(2,2-dimethyl-1,3-dioxolan-4-ylmethyl) carbodiimide (BDDC).

Examples of carbodiimidazoles as the condensing agent include 1,1'-carbonyldiimidazole (CDI), 1,1'-carbonyldi(1,2,4-triazole) (CDT), and 1,1'-oxalyldiimidazole.

Examples of phosgene derivatives as the condensing agent include bis(pentafluorophenyl) carbonate, di-2-pyridyl carbonate, di(N-succinimidyl) carbonate, thiophosgene, triphosgene, and O,O'-di-2-pyridyl thiocarbonate.

Examples of phosphonium-based dehydration condensation agents as the condensing agent include (benzotriazol-1-yloxy)tris-(dimethylamino)phosphonium (BOP), benzotriazol-1-yloxytris(pyrrolidino)phosphonium hexafluorophosphate (PyBOP), bromotris(dimethylamino) phosphonium hexafluorophosfphate (BroP), bromotris(pyrrolidino)phosphonium hexafluorophosphate (PyBroP), (7-azabenzotriazol-1-yloxy)tris(pyrrolidino)phosphonium hexafluorophosphate (PyAOP), and chloro-tris-pyrrolidino-phosphonium hexafluorophosphate (PyCloP). These are collectively called "BOP reagents".

Examples of uronium-based dehydration condensation agents as the condensing agent include (1-cyano-2-ethoxy-2-oxoethylideneaminooxy)dimethylamino-morpholino-carbenium hexafluorophosphate (COMU), 2-(1H-benzotriazol-1-yl)-1,1,3,3 hexafluorophosphate (HBTU), 2-(7-azabenzotriazol-1-yl)-1,1,3,3 hexafluorophosphate (HATU), 2-(1H-benzotriazol-1-yl)-1,1,3,3-tetramethyluroniumtetrafluoroborate (TBTU), 2-(5-norbornene-2,3-dicarboxyimide)-1,1,3,3-tetramethyluronium tetrafluoroborate (TNTU), and O—(N-succinimidyl)-1,1,3,3-tetramethyluronium tetrafluoroborate (TSTU).

Examples of triflate reagents as the condensing agent include 2-[N,N-bis(trifluoromethanesulfonyl)amino]-5-chloropyridine, N-(2-pyridyl)bis(trifluoromethanesulfonimide), trifluoromethanesulfonate 4-nitrophenyl, N-phenylbis(trifluoromethanesulfonimide), trifluoromethanesulfonyl chloride, trifluoromethanesulfonic anhydride, trifluoromethanesulfonanilide, and 1-(trifluoromethanesulfonyl)imidazole.

To promote condensation by the condensing agent and suppress side reaction, a highly nucleophilic additive is preferably used in addition to the condensing agent. Examples of such a highly nucleophilic additive include 1-hydroxybenzotriazole (HOBt), 1-hydroxy-7-aza-benzotriazole (HOAt), 4-(dimethylamino)pyridine (DMAP), ethyl 2-cyano-2-(hydroxyimino)acetate (Oxyma), N-hydroxysuccinimide (HOSu), 6-chloro-1-hydroxy-benzotriazole (Cl-HoBt), and N-hydroxy-3,4-dihydro-4-oxo-1,2,3-benzotriazine (HOOBt).

Esterification Reaction Solution Containing Esterifying Agent

The esterifying agent contained in the esterification reaction solution is not limited, and alkylating agents are preferred among esterifying agents; methylating agents, ethylating agents, propylating agents such as isopropylating agents, butylating agents such as tert-butylating agents, and benzylating agents are more preferred; and methylating agents and ethylating agents are even more preferred.

Examples of methylating agents as the esterifying agent include bromomethane, dimethyl carbonate, dimethyl sulfate, N,N-dimethylformamide dimethylacetal, N,N'-diisopropyl-O-methylisourea, methyl fluorosulfonate, iodomethane, methyl methanesulfonate, 1-methyl-3-p-tolyltriazene, trimethyl orthoformate, tetramethylammonium chloride, methyl p-toluenesulfonate, tetramethylammonium hydroxide 3-(trifluoromethyl)phenyltrimethylammonium hydroxide, trimethyloxonium tetrafluoroborate, trimethylsulfonium hydroxide, and methyl trifluoromethanesulfonate.

Examples of ethylating agents as the esterifying agent include bromoethane, diethyl carbonate, diethyl sulfate, N,N-dimethylformamide diethylacetal, 1-ethyl-3-p-tolyltriazene, O-ethyl-N,N'-diisopropylisourea, iodoethane, ethyl methanesulfonate, triethyl orthoformate, ethyl trifluoromethanesulfonate, and triethyloxonium tetrafluoroborate.

Examples of propylating agents as the esterifying agent include 1-bromopropane, 2-bromopropane, N,N-dimethylformamide dipropylacetal, dipropyl sulfate, diisopropyl sulfate, 1-iodopropane, 2-iodopropane, 1-isopropyl-3-p-tolyltriazene, isopropyl methanesulfonate, triisopropyl orthoformate, propyl methanesulfonate, and O,N,N'-triisopropylisourea.

Examples of butylating agents as the esterifying agent include 1-bromobutane, 2-bromo-2-methylpropane, 2-iodo-2-methylpropane, tert-butyl 2,2,2-trichloroacetimidate, O-tert-butyl-N,N'-diisopropylisourea, N,N-dimethylformamide dibutylacetal, N,N-dimethylformamide di-tert-butylacetal, dibutyl sulfate, 1-iodobutane, and tributyl orthoformate.

Examples of benzylating agents as the esterifying agent include benzyl bromide, benzyl chloride, 1-benzyl-3-p-tolyltriazene, benzyl 2,2,2-trichloroacetimidate, benzyl 2,2,2-trifluoro-N-phenylacetimidate, and O-benzyl-N,N'-diisopropylisourea.

Examples of the esterifying agent include, in addition to the above-mentioned esterifying agents, any alkylating agent.

The esterification reaction solution preferably contains a triazene derivative. The triazene derivative contained in the esterification reaction solution is preferably 1-methyl-3-p-tolyltriazene (MTT), 1-ethyl-3-p-tolyltriazene (ETT), 1-isopropyl-3-p-tolyltriazene, 1-benzyl-3-p-tolyltriazene, or 1-(4-nitrobenzyl)-3-p-tolyltriazene, and more preferably MTT or ETT.

The esterifying agent is not limited to those mentioned above, and the esterification reaction solution can contain any esterifying agent such as 2-chloroethyl methanesulfonate, N,N-dimethylformamide dineopentylacetal, and diamyl sulfate. The esterification reaction solution may contain a salt of any of the above-mentioned esterifying agents.

Concentrations of Alcohol or Esterifying Agent, Etc., in Esterification Reaction Solution In the esterification reaction, it is preferable that a concentration of the alcohol or esterifying agent, or the like to be used be adjusted so that at least one of α2,3-sialic acid, α2,8-sialic acid, and α2,9-sialic acid can be esterified. For linkage-specific modification, it is preferable that a concentration of the alcohol or esterifying agent, or the like to be used be adjusted so as to esterify α2,6-sialic acid. Because linkage-specific modification can be achieved even if all the sialic acids of the glycan in the sample are esterified, the concentration of the alcohol, the condensing agent or additive, or the esterifying agent in the esterification reaction solution can be set high, unless any disadvantage is caused in other aspects.

In an example in which the esterification reaction is performed with an esterifying agent, the concentration of the esterifying agent such as MTT and ETT is preferably 10 mM to 10 M, more preferably 50 mM to 5 M, and even more preferably 100 mM to 1 M. In the case that the esterification reaction is performed with an alcohol, the concentration of the condensing agent can be, for example, 1 mM to 5 M. In the case that a condensing agent and an additive are used in combination, each of the concentrations can be in the above-mentioned range. The alcohol concentration is preferably 0.01 to 20 M, and more preferably 0.1 M to 10 M. The reaction temperature is preferably around −20° C. to 100° C., and more preferably −10° C. to 50° C.

Phase for Esterification Reaction

The esterification reaction can be performed in any of a liquid phase and a solid phase. The state of the sample in causing the esterification reaction is not limited as long as the state allows the sample to be in contact with the esterification reaction solution.

If the reaction is performed in a solid phase, the solid phase carrier for use is not limited as long as the solid phase carrier is capable of immobilizing a glycan, a glycopeptide, a glycoprotein, or the like. To immobilize a glycopeptide or a glycoprotein, for example, a solid phase carrier having, as a ligand, an epoxy group, a tosyl group, a carboxy group, an amino group, or the like can be used. To immobilize a glycan, a solid phase carrier having, as a ligand, a hydrazide group, an aminooxy group, or the like can be used. It is also preferable to allow the glycan to be adsorbed on a carrier, in other words, a stationary phase for hydrophilic interaction chromatography (HILIC), and it is more preferable that the HILIC carrier include an amide group.

Reacting in a state in which the sample is immobilized to a solid phase carrier facilitates removal of the reaction solution and desalting and purification, and sample preparation can be simplified. If the sample in the state of glycoprotein or glycopeptide is immobilized to a solid phase carrier, cleavage with glycosidase such as PNGase F after the esterification reaction allows the sample after the esterification reaction to be collected as a free glycan. If the glycan is immobilized to a solid phase carrier having a hydrazide group, an aminooxy group, or the like as a ligand, the sample after the esterification reaction can be released and collected by using acid treatment or the like.

As necessary, the sample after the esterification reaction may be subjected to treatments such as purification, desalting, and solubilization, for example, by using a known method or the like. The same is applied before and after amidation reaction described later.

In releasing the sample from a solid phase carrier after the esterification reaction, conditions described later in relation to amidation reaction may be employed. Reacting in a state in which the sample is immobilized to a solid phase carrier facilitates, for example, removal of the esterification reaction solution after the esterification reaction, which allows efficient modification of sialic acid.

The completion of step S1003 is followed by step S1005.

Amidation Reaction

In step S1005, amidation reaction is performed (hereinafter, the expression "amidation reaction" refers to the amidation reaction in step S1005, unless otherwise stated) that amidates a sialic acid modified by the esterification in step S1003 through contacting the sample with a reaction solution (hereinafter, referred to as "amidation reaction solution"). In the amidation reaction, the esterified form is converted into the amidated form (hereinafter, appropriately called ester-to-amide conversion) in a sialic acid esterified in step S1003. In the amidation reaction, at least one of α2,3-sialic acid, α2,8-sialic acid, and α2,9-sialic acid, in particular, at least one of α2,3-sialic acid and α2,8-sialic acid is amidated.

The present inventors have found a method for directly and quickly amidating ester formed in sialic acid, which is quite contrast to the common general knowledge where a carboxy group of sialic acid is amidated by addition of a solution containing a dehydration condensation agent and an amine or the like to a sample. Moreover, surprisingly, this direct amidation provides reaction efficiencies different between the case for sialic acids of some linkage types, such as α2,3-sialic acid and α2,8-sialic acid, and sialic acids of other linkage types, such as α2,6-sialic acid. Accordingly, linkage-specific modification can be achieved by performing amidation reaction of a glycan including an esterified sialic acid of such a linkage type.

In addition, as demonstrated in NPTL 2, a lactonized sialic acid can also be quickly amidated with the amidation reaction solution in the present embodiment. Accordingly, even α2,3-, α2,8-, or α2,9-sialic acid lactonized through the esterification reaction in step S1003 is amidated with the amidation reaction solution in the same manner as for esterified one. Therefore, it is preferable not to perform an operation to cleave a lactone structure formed through the esterification reaction before the amidation reaction.

In the method as described in NPTL 4, for example, use of methanol in place of ethanol in first-stage esterification of α2,6-sialic acid leads to a higher reaction rate of esterification, causing not only lactonization but also methyl-esterification to α2,3-sialic acid, which makes it impossible to distinguish from α2,6-sialic acid. Even in such cases, the method in the present embodiment can achieve amidation of both of the methyl-esterified sialic acid and lactonized sialic acid. Hence, the method in the present embodiment enables more reliable linkage-specific modification of sialic acid.

When reference is made to a lactone formed in a sialic acid in the present and subsequent embodiments, the term refers to a lactone formed between a sialic acid and a monosaccharide adjacent to the sialic acid, and a lactone formed, for example in the inside of a sialic acid.

The amidation reaction solution contains a reactant containing ammonia, amine, or a salt thereof to be reacted with a sialic acid modified through the esterification (hereinafter, referred to as the amidation reactant). The amidation reactant is used for the purpose of modifying through amidation caused by the process that at least a part of a molecule of the amidation reactant bonds to a sialic acid. The amidation reactant is, for example, a nucleophilic agent. The amidation reaction is preferably performed only through contacting the sample with the amidation reaction solution, and thus lactones can be stabilized through a simple operation.

Although the amidation reaction does not require any dehydration condensation agent and may contain no dehydration condensation agent, the amidation reaction solution may contain a dehydration condensation agent. For example, the amidation reaction solution may be prepared by adding ammonia, an amine, or a salt thereof to the sample without removing the esterification reaction solution added to the sample in step S1003. In this way, the amidation reaction can be performed through a simple operation. Alternatively, after an operation to remove the esterification reaction solution added to the sample in step S1003, the amidation reaction is performed only through contacting the sample with the amidation reaction solution. In the amidation reaction, an operation of reacting the sample with a dehydration condensation agent can be omitted after contacting the sample with the amidation reaction solution. However, this operation may be performed, for example, for another purpose.

In the case that an analysis sample obtained by using the method for preparing an analysis sample in the present embodiment is analyzed through mass spectrometry, selection is made for the alcohol or esterifying agent to be contained in the esterification reaction solution and the amidation reactant so that the modified product as ester formed through the esterification reaction and the modified product as amide formed through the amidation reaction are different in mass. Selection is made for the alcohol or esterifying agent to be contained in the esterification reaction solution and the amidation reactant so that accurate mass separation reasonable for the mass resolution of mass spectrometry is achieved for the two modified forms obtained. To clearly distinguish the two modified products from each other by single mass spectrometry, it is preferable to provide enough mass difference with use of combination, for example, of methyl ester/ethyl amide or ethyl ester/methyl amide, or increase mass difference with use of stable isotope labels.

Combination of the modified product as ester formed through the esterification reaction and the modified product as amide formed through the amidation reaction may be appropriately changed according to the sample to be used. For example, there exists not only the sialic acid Neu5Ac, which is a representative sialic acid, but also the sialic acid Neu5Gc, which has a molecular weight 16 Da higher than that of Neu5Ac. Since these sialic acids can exist as a mixture, in the case of disialylated biantennary glycans, for example, there exist three combinations of sialic acids, namely, Neu5Ac x2, Neu5Ac+Neu5Gc, and Neu5Gc x2 (hereinafter, x2 indicates including two identical sialic acids). If methyl-esterification and ethylamidation are performed for a sample in which they are present as a mixture, nine peaks shown in Table 1 in the following may be detected (Table 1 and Table 2 below show mass differences with reference to the case of Neu5Ac x2, α2,6-x2).

TABLE 1

|  | α2,6-x2 | α2,6-+α2,3- | α2,3-x2 |
|---|---|---|---|
| Neu5Ac x2 | 0 | +13 | +26 |
| Neu5Ac + Neu5Gc | +16 | +29 | +42 |
| Neu5Gc x2 | +32 | +45 | +58 |

Here, +13 and +16, +26 and +29, +29 and +32, and +42 and +45 are each a pair of close masses. In additionally considering isotope distribution, peaks corresponding to each pair are detected in a partially overlapped manner, which may disable accurate data analysis. In such a case, overlap of peaks is prevented by performing amidation after the methyl-esterification with use of propylamine as the amidation reactant, and thus accurate data analysis can be achieved. If methyl-esterification and propylamidation are performed for a sample in which three combinations of Neu5Ac x2, Neu5Ac+Neu5Gc, and Neu5Gc x2 are present as a mixture, nine peaks shown in Table 2 in the following may be detected.

TABLE 2

|  | α2,6-x2 | α2,6-+α2,3- | α2,3-x2 |
| --- | --- | --- | --- |
| Neu5Ac x2 | 0 | +27 | +54 |
| Neu5Ac + Neu5Gc | +16 | +43 | +70 |
| Neu5Gc x2 | +32 | +59 | +86 |

In this case, peaks are separated in a preferred manner. The same also holds true for glycans including three or more sialic acids. Thus, a combination of esterification and amidation can be appropriately selected according to the complexity of a glycan contained in a sample.

In the case that an analysis sample obtained by using the method for preparing an analysis sample in the present embodiment is analyzed through chromatography, selection is made for the alcohol or esterifying agent to be contained in the esterification reaction solution and the amidation reactant so that accurate separation reasonable for the resolution of chromatography can be achieved for the two modified products obtained.

Amine in Amidation Reaction

In the present and subsequent embodiments, the term "amine" is intended to include hydrazine, hydrazine derivatives, and hydroxyamine, and not to include ammonia and salts of ammonia. If an amine is used for the amidation reaction, the amine included in the amidation reactant is preferably at least one compound selected from the group consisting of primary amines, hydrazine, hydrazine derivatives, and hydroxyamine, and salts thereof. The carboxy group of α2,3-sialic acid and the like is present at a position causing relatively high steric hindrance as compared with the carboxy group of α2,6-sialic acid, and hence primary amines are expected to selectively react with α2,3-sialic acid and the like more readily than other amines.

In using a primary amine for the amidation reactant, primary amines in which one or no carbon atom is directly bonding to a carbon atom bonding to an amino group are more preferred. The reason is that even when the carbon chain has a branch, lowering of efficiency of the amidation reaction can be reduced in this case, in which the branch is present at a position distant from the amino group.

For the amidation reactant, a primary amine having a linear hydrocarbon group is preferred, and a primary amine having a linear alkyl group is even more preferred. The primary amine having a linear alkyl group as the amidation reactant is preferably a primary amine having 10 or less carbon atoms, more preferably a primary amine having six or less carbon atoms, specifically, methylamine, ethylamine, propylamine, butylamine, pentylamine, or hexylamine, and the most preferably methylamine. It is preferable for the amine contained in the amidation reaction solution to have a linear structure without any branch (hereinafter, "branch" refers to a branch of a hydrocarbon chain), or have a smaller number of carbon atoms, because the esterified sialic acid is more efficiently amidated.

The hydrazine derivative contained in the amidation reactant is not limited. In the present and subsequent embodiments, hydrazide derivatives include hydrazides such as acetohydrazide, hydrazide acetate, benzohydrazide, and hydrazide benzoate, and may be used for the amidation reactant. The hydrazine derivative included in the amidation reactant can be at least one compound selected from the group consisting of methylhydrazine, ethylhydrazine, propylhydrazine, butylhydrazine, phenylhydrazine, and benzylhydrazine, and acetohydrazide, hydrazide acetate, benzohydrazide, and hydrazide benzoate. The hydrazine or hydrazine derivative as the amidation reactant is preferably hydrazine or methylhydrazine in order to enhance or maintain the efficiency of the amidation reaction.

If a primary amine having an unsaturated chain hydrocarbon group is used for the amidation reactant, the unsaturated chain hydrocarbon group preferably includes a double bond, and more preferably includes an allyl group, and the amine is even more preferably allylamine. A primary amine including a hydroxy group may be used for the amidation reactant, and in this case ethanolamine is preferred. The amine contained in the amidation reaction solution may include various functional group(s) other than alkyl groups. When a glycan is modified so as to be provided with such a functional group as a result of the amidation reaction, the modified glycan can be separated more easily not only through mass spectrometry but also through chromatography or the like.

The amidation reactant can contain a salt of ammonia or any of the amines described above for the amidation reactant. Examples of salts of ammonia or any of the amines contained in the amidation reaction solution include inorganic salts and organic salts of ammonia or any of the amines, and inorganic salts such as carbonates, hydrochlorides, nitrates, sulfates, phosphates, and methanesulfonates are preferred; carbonates, hydrochlorides, and nitrates are more preferred; and hydrochlorides are even more preferred. Preferred as a hydrochloride of a primary amine having a linear hydrocarbon group are methylamine hydrochloride, ethylamine hydrochloride, propylamine hydrochloride, butylamine hydrochloride, and pentylamine hydrochloride, and more preferred are methylamine hydrochloride and ethylamine hydrochloride.

Concentration of Amidation Reaction Solution

The concentration of the amidation reactant such as methylamine or ethylamine in the amidation reaction solution is preferably 0.01% or more, more preferably 0.1% or more, and even more preferably 1% or more on wt/vol % basis. The higher the concentration of the amidation reactant in the amidation reaction solution is, the more reliably the esterified sialic acid can be amidated. The concentration of the amidation reactant such as methylamine or ethylamine in the amidation reaction solution is preferably less than 40%, and more preferably less than 20% on wt/vol % basis. This can suppress unintended reaction due to high concentration, and suppress amidation of α2,6-sialic acid to facilitate linkage-specific modification.

Solvent of Amidation Reaction Solution

The solvent of the amidation reaction solution is preferably an aqueous solvent, an organic solvent, or a mixed solvent of an aqueous solvent and an organic solvent, in order to cause amidation reliably. The solvent of the amidation reaction solution may be, for example, water, an alcohol such as methanol or ethanol, dimethyl sulfoxide (DMSO), or acetonitrile, or a liquid mixture of them. In modifying α2,6-sialic acid and other sialic acids in a linkage-specific manner, it is preferable for the solvent of the amidation reaction solution to contain an organic solvent in order to prevent amidation of α2,6-sialic acid.

pH of Amidation Reaction Solution

The pH of the amidation reaction solution is 7.7 or higher. The pH of the amidation reaction solution is preferably 8.0 or higher, more preferably 8.8 or higher, and even more preferably 10.3 or higher. Higher pH is preferred for the amidation reaction solution because side reaction such as hydrolysis is suppressed and the esterified sialic acid is more reliably amidated with use of any of various amidation reactants.

Time Needed for Amidation Reaction

The amidation reaction is completed within several seconds to several minutes. Thus, the time during which the sample is in contact with the amidation reaction solution in order to amidate the esterified sialic acid through the amidation reaction (hereinafter, referred to as "reaction time") is preferably shorter than 1 hour, more preferably shorter than 30 minutes, even more preferably shorter than 15 minutes, further preferably shorter than 5 minutes, and the most preferably shorter than 1 minute. It is preferable to wash the sample with the amidation reaction solution, or only to temporarily pass the amidation reaction solution through the sample held on a carrier or the like. The time during which the sample is in contact with the amidation reaction solution is not limited, and can be, for example, appropriately 0.1 seconds or longer or 1 second or longer in order to sufficiently complete the reaction. Alternatively, the sample and the amidation reaction solution may be mixed together and directly subjected to evaporation to dryness without providing any reaction time. Through setting the reaction time of the amidation reaction short, analysis of the sample becomes more efficient.

Phase for Amidation Reaction

The state of the sample in causing the amidation reaction is not limited as long as the state allows the sample to be in contact with the amidation reaction solution, and may be a solid phase or a liquid phase. In performing the amidation reaction in a liquid phase, the amidation reaction solution may be added to the sample with the solution after the esterification reaction left as it is, as described above, or known pretreatment such as purification, desalting, or solubilization may be performed after the esterification reaction. In performing the amidation reaction with the sample immobilized to a solid phase, the sample subjected to the esterification reaction in a solid phase may be subjected to the amidation reaction in a state in which immobilization to the solid phase is maintained. Alternatively, the sample after being subjected to the esterification reaction may be immobilized to a solid phase and subjected to the amidation reaction.

If the amidation reaction is performed in a solid phase, the solid phase carriers described above for the esterification reaction can be used. In immobilizing the sample to a solid phase carrier, the conditions described above for the esterification reaction can be used. If the amidation reaction is performed in a solid phase, after the sample immobilized to the solid phase carrier is subjected to the action of the amidation reaction solution for amidation, the sample can be suitably released and collected from the carrier, for example, through a chemical technique or enzyme reaction. For example, a glycoprotein or a glycopeptide immobilized to the carrier may be enzymatically cleaved by using glycosidase such as PNGase F or a digestive enzyme such as trypsin, and a glycan bonding to a solid phase carrier having a hydrazide group may be released by using a weakly acidic solution and collected. In HILIC, the amidation reaction can be performed with an amidation reaction solution containing acetonitrile or the like as a solvent followed by elution with an aqueous solution such as water.

The completion of step S1005 is followed by the initiation of step S1007. In step S1007, an analysis sample is prepared. The method for preparation of an analysis sample is not limited and may be any method with which an analysis sample containing the glycan having been subjected to the amidation reaction in step S1005 for analysis in step S1009 can be obtained.

If mass spectrometry with matrix-assisted laser desorption/ionization (MALDI) is performed in step S1009, for example, an analysis sample is prepared as follows. A solution containing the sample obtained after the amidation reaction is added dropwise onto a sample plate for MALDI, a solution containing a matrix is added dropwise to the solution on the plate, and the resultant is dried. Thereby, a mixed crystal of the sample and the matrix can be obtained as a mass spectrometry sample. In the preparation of a mass spectrometry sample, a solution containing the sample and a solution containing the matrix may be mixed together and then added to a sample plate for MALDI, the order of dropwise addition of these solutions may be changed, and an additive for the matrix may be further used. If another type of analysis such as chromatography is performed, an analysis sample is prepared, for example, by using a known method or the like.

In the analysis sample obtained by using the above-described preparation method, an esterified form has been formed in α2,6-sialic acid through the esterification reaction. In α2,3-, α2,8-, and α2,9-sialic acids, in particular, in α2,3- and α2,8-sialic acids, an esterified form, which was formed through the esterification reaction, has been converted into an amidated form through the amidation reaction.

The completion of step S1007 is followed by the initiation of step S1009.

In step S1009, the analysis sample is analyzed. It is preferable that the analysis sample be analyzed through at least one of mass spectrometry and chromatography.

Through the above-described esterification reaction and amidation reaction, glycans modified in the reactions have different masses. Accordingly, these glycans can be separated through mass spectrometry on the basis of the linkage type of sialic acid.

The ionization method in the mass spectrometry is not limited, and MALDI, electrospray ionization (ESI), nano-electrospray ionization (nano-ESI), or the like can be used. MALDI is particularly preferred for the ionization method. In ionization in the mass spectrometry, any of a positive ion mode or a negative ion mode may be used. The mass spectrometry may be single mass spectrometry or performed in multiple stages, which suitably allows analysis of the structure of a glycan in addition to the linkage type of sialic acid, or the structure of a peptide chain. At least one or more of arbitrary mass analyzers such as quadrupole, ion trap, and time-of-flight mass analyzers can be combined for use in the mass spectrometer. Dissociation of an ion or addition or the like of an atom or atomic group to an ion can be appropriately performed.

If analysis is performed through chromatography, liquid chromatography is preferable. The column for liquid chromatography is not limited, and a hydrophobic reverse phase column such as C30, C18, C8, or C4, a carbon column, a normal phase column for HILIC, or any other column can be appropriately used. It is preferable for a precise analysis of components in the sample through multiple operations of separation to make measurement by using liquid chromatography/mass spectrometry (LC/MS).

The data acquired through mass spectrometry or chromatography are analyzed, and, for example, sialic acids in glycans contained in the sample are analyzed. This data analysis enables, for example, estimation of structures of glycans, including the linkage type of sialic acid. The analysis method for the data acquired through mass spectrometry or chromatography is not limited.

At the completion of step S1009, the procedure is terminated.

Suppression of Side Reaction of Glycopeptide and Glycoprotein

In the case that the esterification reaction solution and amidation reaction solution are added to a glycopeptide or a glycoprotein to modify sialic acids as described above, side reaction may occur, such as intramolecular dehydration condensation between an amino group and a carboxy group present in the side chain of an amino acid or at an end of the peptide backbone in the glycopeptide or glycoprotein. In this case, preliminary blocking of amino groups, for example, by using chemical modification, before modification of sialic acids can suppress the side reaction of a peptide moiety in modification of sialic acids. For the details, see the following literature: Takashi Nishikaze, Sadanori Sekiya, Shinichi Iwamoto, Koichi Tanaka. "A Universal Approach to linkage-Specific Derivatization for Sialic Acids on Glycopeptides," Journal of The American Society for Mass Spectrometry, June, 2017, Volume 28, Issue 1 Supplement, Poster No. MP091. For example, a glycopeptide or a glycoprotein can be subjected to reaction to block amino groups such as dimethyl labeling and guanidinylation, and then to esterification reaction and amidation reaction.

Kit for Preparing Analysis Sample

Provided is a kit for preparing an analysis sample (hereinafter, referred to as "preparation kit") which is suitably used for the method for preparing an analysis sample in the present embodiment.

Figure 2:
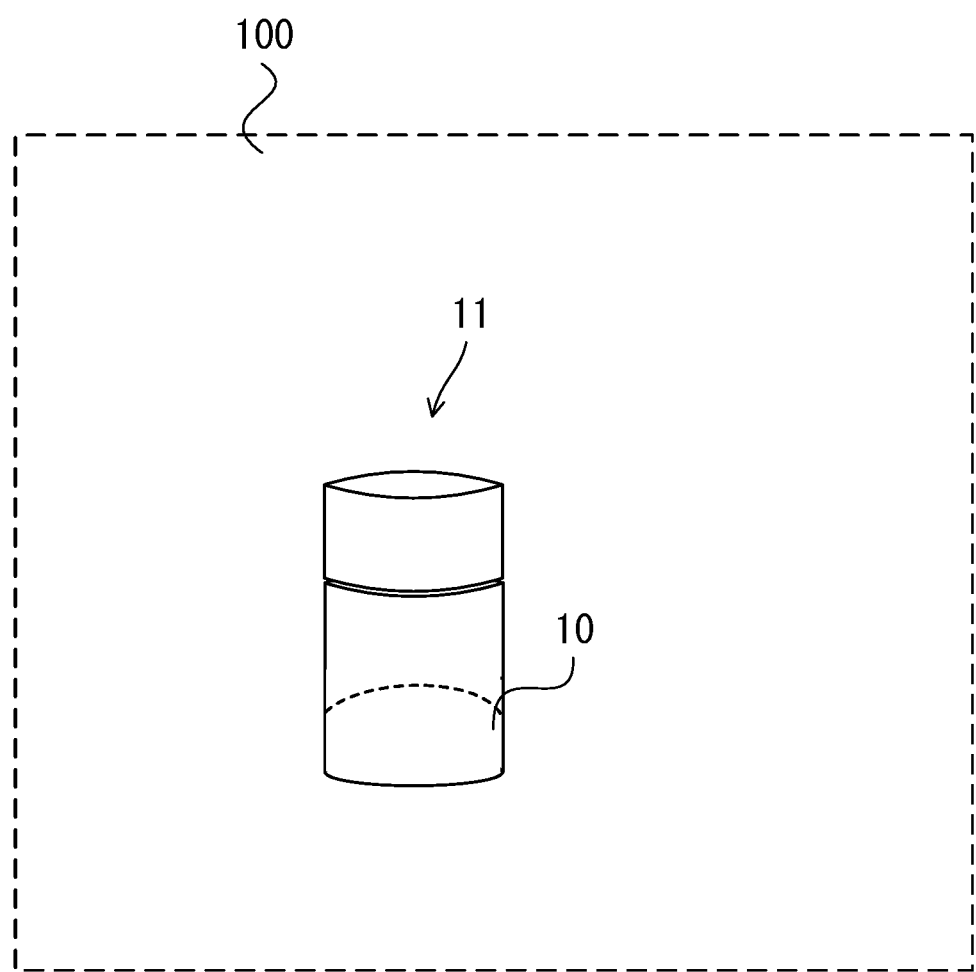
FIG. 2 shows a conceptual diagram illustrating a kit for preparing an analysis sample.

FIG. 2 shows a conceptual diagram of a preparation kit 100 in the present embodiment. In the example in FIG. 2, the preparation kit 100 includes an esterifying agent 10 for the esterification reaction. The esterifying agent 10 is contained in a container 11. The capacity, shape, and so on of the container 11 are not limited. The preparation kit 100 can include a regent or any consumable other than reagents for the above analysis, or a document, for example, describing a protocol to prepare an analysis sample in the present embodiment or showing, for example, a URL of a website describing the protocol. The preparation kit 100 can include, for example, reagents contained in the esterification reaction solution such as an alcohol, a condensing agent, an additive, and an esterifying agent, and at least one compound selected from the group consisting of ammonia, an amine, hydrazine, a hydrazine derivative, and hydroxyamine, and salts thereof to be reacted with sialic acids modified through esterification. By using the preparation kit 100, an analysis sample can be more efficiently prepared.

Modifications as shown below also fall within the scope of the present invention, and can be combined with the above-described embodiment. In Variations below, a part or the like having the same structure or function as in the above-described embodiment is referred to with the same reference sign, and description thereof is omitted as appropriate.

Variation 1

In the above-described embodiment, analysis of the sample obtained after the esterification reaction may be performed in addition to analysis of the sample obtained after the amidation reaction. The analysis of the sample obtained after the amidation reaction is referred to as the first analysis, and the analysis of the sample obtained after the esterification reaction is referred to as the second analysis.

Figure 3:
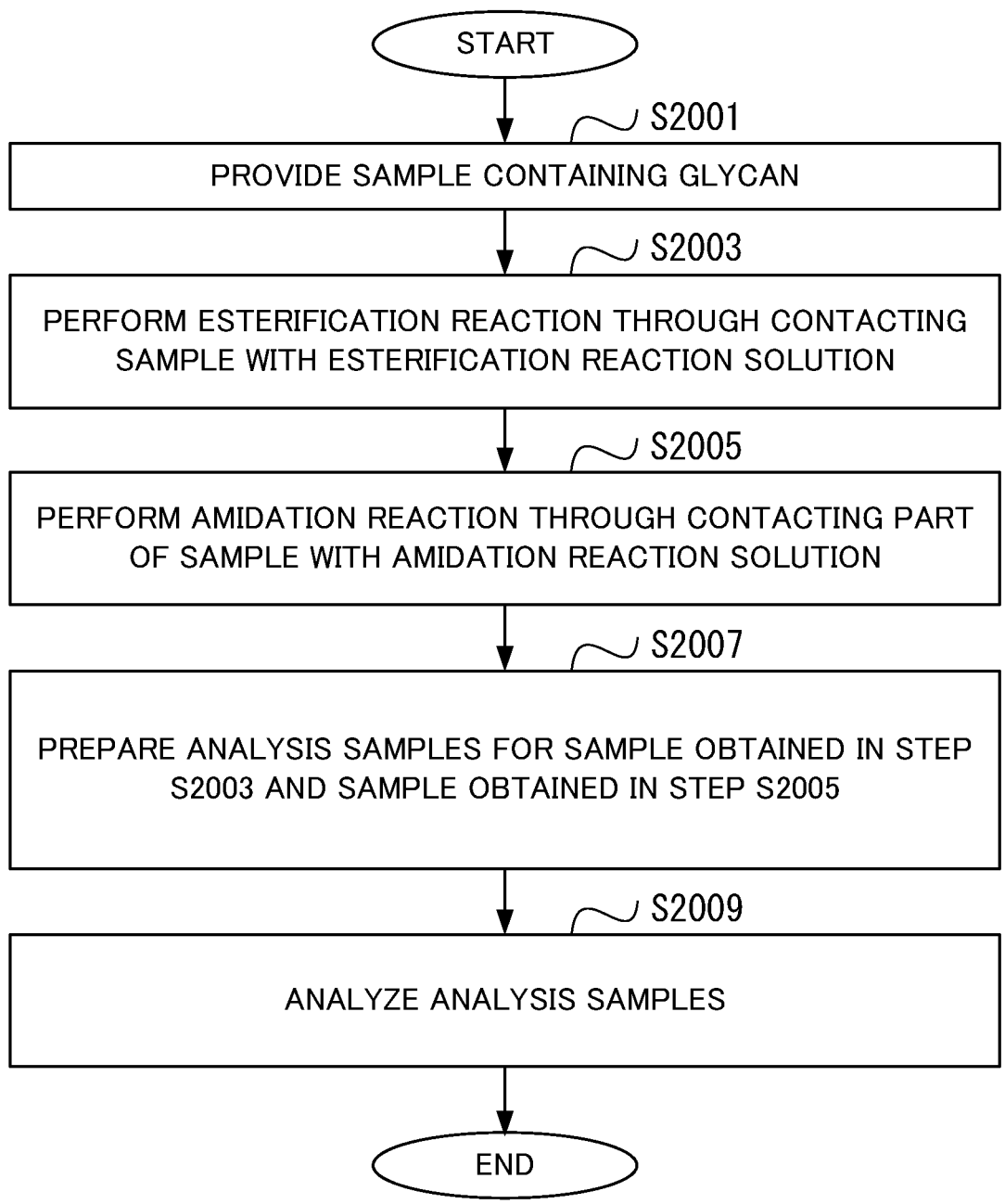
FIG. 3 shows a flowchart illustrating the procedure of an analysis method according to a Variation.

FIG. 3 shows a flowchart illustrating the procedure of an analysis method according to the method for preparing an analysis sample in the present Variation. Steps S2001 and S2003 are the same as steps S1001 and S1003 in the above-described embodiment, and hence description is omitted. The completion of step S2003 is followed by the initiation of step S2005.

In step S2005, amidation reaction is performed through contacting a part of the sample with an amidation reaction solution. The solution containing the sample obtained in step S2003 is separated into multiple parts by aliquoting or the like, and a part of the solution can be subjected to amidation reaction with use of the same amidation reaction solution under the same conditions as in the above-described embodiment. The completion of step S2005 is followed by the initiation of step S2007.

In step S2007, analysis samples are prepared for the sample obtained in step S2003 and the sample obtained in step S2005. The analysis sample for the first analysis that is prepared with use of the sample after being subjected to the amidation reaction is defined as the first analysis sample, and the analysis sample for the second analysis that is prepared with use of the sample after being subjected to the esterification reaction is defined as the second analysis sample. The first analysis sample and second analysis sample are prepared by using a known method or the like, as with the case of the method for preparing an analysis sample in the above-described embodiment. The completion of step S2007 is followed by the initiation of step S2009.

In step S2009, the analysis samples are analyzed. The first analysis for the first analysis sample and the second analysis for the second analysis sample are performed. It is preferable that the first analysis and the second analysis be performed through the same analysis method. For example, the first analysis and second analysis are both performed through mass spectrometry, both performed through chromatography, or both performed through LC/MS. This enables data analysis based on comparison between data acquired in the first analysis and data acquired in the second analysis. In the case that the first analysis and second analysis are performed through mass spectrometry, for example, it follows that peaks for a glycan including α2,3-sialic acid in a mass spectrum acquired in the second analysis are shifted in a mass spectrum acquired in the first analysis by m/z corresponding to mass change in conversion from an esterified form into an amidated form. Thus, more precise glycan analysis, such as identification of a peak, can be performed on the basis of difference between data acquired in the first analysis and data acquired in the second analysis and information on mass change associated with conversion from an esterified form to an amidated form. At the completion of step S2009, the procedure is terminated.

Variation 2

In the above-described embodiment, an example was described in which linkage-specific modification of sialic acids is performed by amidating esterified sialic acids through amidation reaction. However, the above amidation reaction may be used in amidating sialic acid without any purpose of linkage-specific modification.

Variation 3

More surprisingly, the present inventors found that in the above-described amidation reaction, structure-specific amidation of sialic acid in a glycan can be achieved based on the composition of the solvent of the amidation reaction solution. This means that in performing amidation reaction in step S1005 in the above-described flowchart of FIG. 1 or step S2005 in the flowchart of FIG. 3, for example, for the same linkage type or different linkage types, selective amidation of sialic acids is achieved on the basis of the position of each sialic acid in a glycan or the structure in the vicinity of each sialic acid in a glycan. Here, "the structure of glycan in the vicinity of each sialic acid" includes a structure associated with a bond between a monosaccharide to which the sialic acid is directly bonding and another saccharide.

The amidation reaction solution in the amidation reaction according to the present Variation preferably contains an organic solvent, and more preferably contains acetonitrile. The concentration of acetonitrile for the solvent of the amidation reaction solution is appropriately adjusted so that sialic acids can be selectively amidated, as described above. The amidation reaction solution more preferably contains 90% or more of acetonitrile, even more preferably 95% or more of acetonitrile, and further preferably 98% or more of acetonitrile on wt/vol % basis as the solvent. It is the most preferable that the solvent of the amidation reaction solution be acetonitrile, that is, consist substantially only of acetonitrile. This enables selective amidation of sialic acids other than α2,6-sialic acid, in particular, α2,3-sialic acid, α2,8-sialic acid, and α2,9-sialic acid, on the basis of the structure of a glycan. In particular, α2,3-sialic acid and α2,8-sialic acid present at an end, in particular, at a non-reducing end of a glycan can be selectively amidated. Other conditions for the amidation reaction of the present Variation can be appropriately selected from conditions used in the above-described embodiment.

More specifically, by subjecting a sample containing a glycan to amidation reaction with an amidation reaction solution containing an organic solvent, in particular, containing acetonitrile, sialic acids under the following conditions are selectively amidated. The conditions are such that to position 4 of a monosaccharide to which a sialic acid other than α2,6-sialic acid, in particular, α2,3- or α2,8-sialic acid, is directly bonding, another monosaccharide is not bonding. Adjustment can be made so that sialic acids that do not satisfy the conditions are not amidated by the amidation reaction solution containing an organic acid such as acetonitrile. The conditions are inferred to be based on the lactone structure of a sialic acid, which is forming a cyclic structure including position 4 of a monosaccharide adjacent to the sialic acid, and hence affects as an intermediate or the like of the amidation reaction.

Figure 4A:
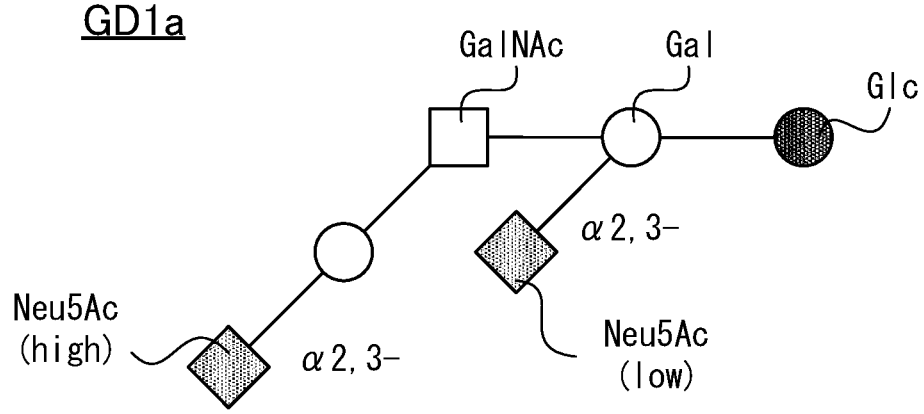
Figure 4B:
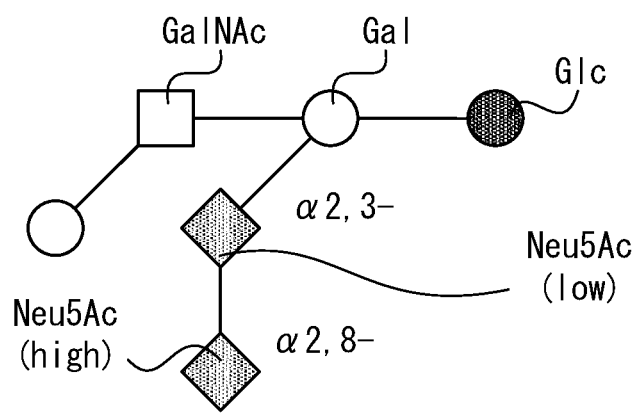
FIG. 4B shows a conceptual diagram illustrating the structure of the glycan GD1b.
Figure 4C:
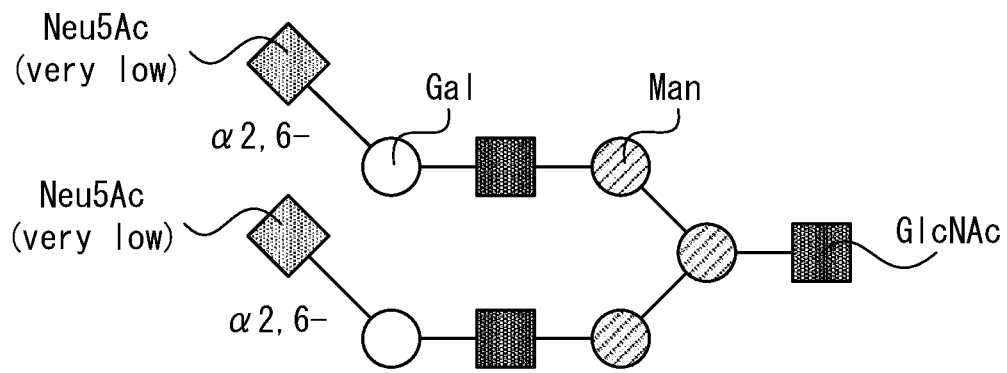
FIG. 4C shows a conceptual diagram illustrating the structure of the glycan A2GN1.

FIGS. 4A, 4B, and 4C each show a conceptual diagram illustrating an example of selectivity in the amidation reaction according to the present Variation. FIGS. 4A and 4B respectively show the structures of the human disialogangliosides GD1a and GD1b, as glycosphingolipids. In FIGS. 4A, 4B, and 4C, a sialic acid that is likely to be amidated is indicated as a reference sign of Neu5Ac (high), a sialic acid that is less likely to be amidated as a reference sign of Neu5Ac (low), and a sialic acid that is extremely less likely to be amidated as a reference sign of Neu5Ac (very low). Sialic acids that are likely to be amidated are amidated by an amidation reaction solution containing an organic solvent such as acetonitrile or an aqueous solvent such as water. Amino acids that are less likely to be amidated are not amidated by an amidation reaction solution containing an organic solvent such as acetonitrile, but amidated by an amidation reaction solution containing an aqueous solvent such as water. Amidation of sialic acids that are extremely less likely to be amidated is difficult unless the concentration of an amidation reactant is set higher than that in amidating other sialic acids.

The glycan GD1a (FIG. 4A) includes a linear chain consisting of glucose (Glc), two galactose (Gal) moieties, and N-acetylgalactosamine (GalNAc), and α2,3-sialic acid bonding to each of the two Gal moieties. The situation that the linkage type of a sialic acid is α2,3- is schematically indicated by drawing the sialic acid in the lower left of Gal to which the sialic acid is bonding (the same is applied to the subsequent drawings). In the amidation reaction according to the present Variation, α2,3-sialic acid (Neu5Ac (high)) bonding to Gal to which no monosaccharide is bonding at position 4 is selectively amidated in the glycan GD1a. In addition, α2,3-sialic acid (Neu5Ac (low)) bonding to Gal to which ne GalNAc is bonding at position 4 can be free from amidation.

The glycan GD1b includes a linear chain consisting of Glc, two Gal moieties, and GalNAc, α2,3-sialic acid bonding to Gal bonding to Glc, and α2,8-sialic acid bonding to this α2,3-sialic acid. The situation that the linkage type of a sialic acid is α2,8- is schematically indicated by drawing the sialic acid directly below a monosaccharide to which the sialic acid is bonding (the same is applied to the subsequent drawings). The glycan GD1a and the glycan GD1b are isomers of each other. In the glycan GD1b (FIG. 4B), α2,8-sialic acid (Neu5Ac (high)) bonding to Neu5 Ac to which no monosaccharide Gal is bonding at position 4 is selectively amidated through the amidation reaction according to the present Variation. In addition, α2,3-sialic acid (Neu5Ac (low)) bonding to Gal to which GalNAc is bonding at position 4 can be free from amidation.

FIG. 4C shows a conceptual diagram illustrating the structure of the glycan A2GN1. The glycan A2GN1 includes a basic structure consisting of N-acetyl-D-glucosamine (GlcNAc) and mannose (Man) and two side chains. To each of the two side chains, GlcNAc, galactose (Gal), and a sialic acid (Neu5Ac) are bonded. The situation that the linkage type of a sialic acid is α2,6- is schematically indicated by drawing the sialic acid in the upper left of Gal to which the sialic acid is bonding (the same is applied to the subsequent drawings). The probability that α2,6-sialic acid is amidated is very low, and amidation through amidation reaction is not easy.

The present Variation is applicable not only to the glycans illustrated in FIGS. 4A, 4B, and 4C, but also to various glycans including glycolipid-type glycans and N-glycans.

Variation 4

In Variation 3 described above, amino acids may be modified in a linkage-specific and structure-specific manner. In the present Variation, α2,6-sialic acid is esterified through esterification reaction. Among sialic acids other than α2,6-sialic acid, those that satisfy the conditions described in Variation 3 are modified through first-stage amidation. This reaction that causes first-stage amidation is referred to as the first amidation reaction, and the amidation reaction solution and the amidation reactant in the first amidation reaction are referred to as the first amidation reaction solution and the first amidation reactant, respectively. Among sialic acids other than α2,6-sialic acid, those that do not satisfy the conditions described in Variation 3 are modified through second-stage amidation. This reaction that causes second-stage amidation is referred to as the second amidation reaction, and the amidation reaction solution and the amidation reactant in the second amidation reaction are referred to as the second amidation reaction solution and the second amidation reactant, respectively. Selection is made for the first amidation reactant and the second amidation reactant so that modified products formed through bonding of them to sialic acids can be distinguishably detected through analysis by mass spectrometry or the like.

Figure 5:
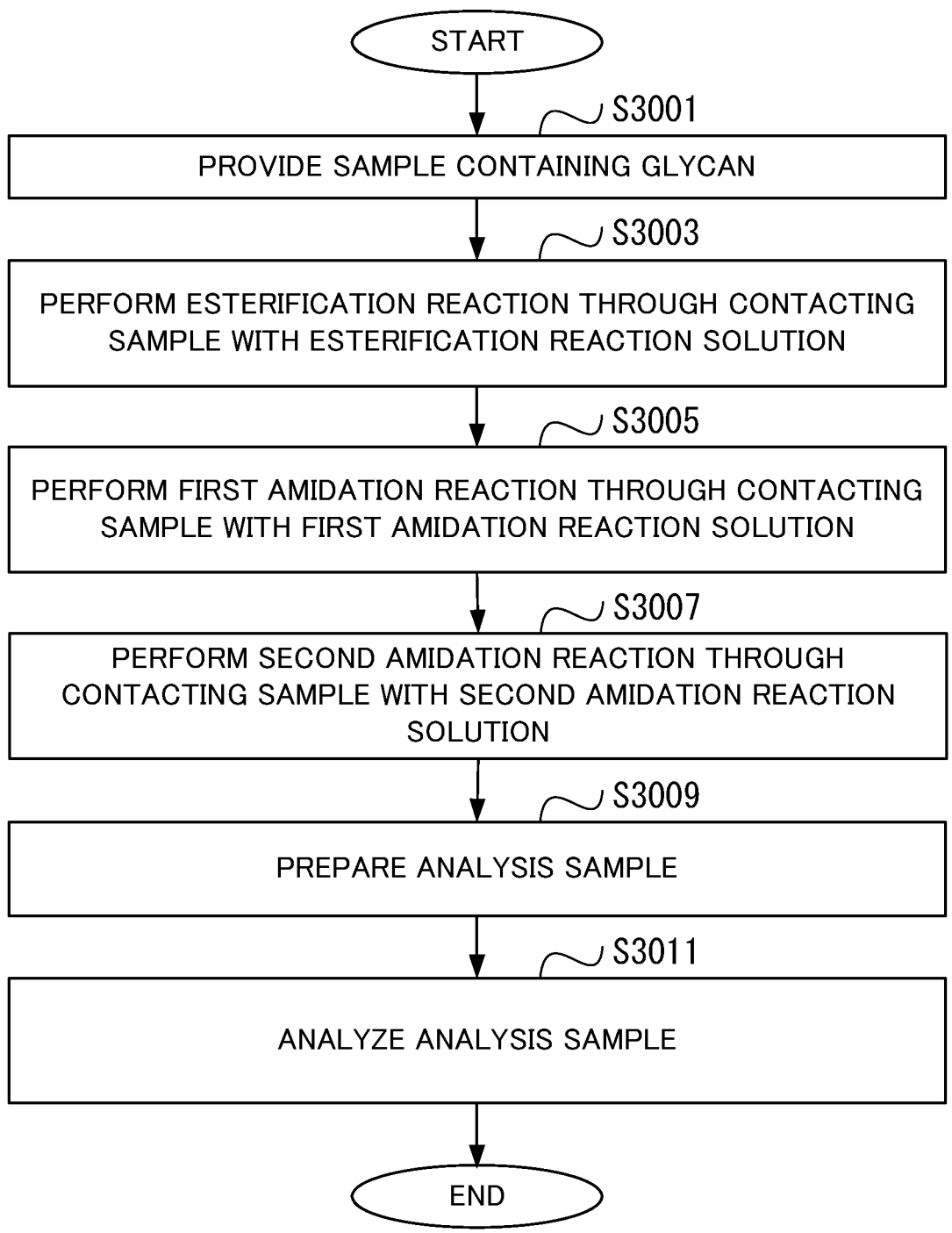
FIG. 5 shows a flowchart illustrating the procedure of an analysis method according to a Variation.

FIG. 5 shows a flowchart illustrating flow of the analysis method of the present Variation. Steps S3001 and S3003 are the same as steps S1001 and S1003 in the flowchart shown in FIG. 1, and hence description thereof is omitted. At least α2,6-sialic acid is esterified through the esterification reaction, and other sialic acids are esterified (or lactonized). The completion of step S3003 is followed by the initiation of step S3005.

In step S3005, the first amidation reaction is performed through contacting the sample with the first amidation reaction solution. The solvent of the first amidation reaction solution contains an organic solvent such as acetonitrile, and, preferably, substantially consists only of an organic solvent such as acetonitrile. It is preferable that the first amidation reaction solution be removed from the sample after the completion of the first amidation reaction, and, in the same manner as after the above-described esterification reaction, other operations such as purification, desalting, solubilization, bonding a glycan to a solid phase carrier, and releasing a glycan from a solid phase carrier can be appropriately performed. Among α2,3-, α2,8-, and α2,9-sialic acids, in particular, among α2,3- and α2,8-sialic acids, those that are present, for example, at a non-reducing end and satisfy the conditions in Variation 3 described above are modified by the first amidation reactant through the first amidation reaction. The completion of step S3005 is followed by the initiation of step S3007.

In step S3007, the second amidation reaction is performed through contacting the sample with the second amidation reaction solution. The solvent of the second amidation reaction solution contains an aqueous solvent such as water. Among α2,3-, α2,8-, and α2,9-sialic acids, in particular, among α2,3- and α2,8-sialic acids, those that do not satisfy the conditions in Variation 3 described above are modified by the second amidation reactant through the second amidation reaction. The completion of step S3007 is followed by the initiation of step S3009. Steps S3009 and S3011 are the same as steps S1007 and S1009 in the flowchart shown in FIG. 1, and hence description thereof is omitted.

Through the analysis method of the present Variation, α2,6-sialic acid and other sialic acids can be distinguishably detected in a linkage-specific manner. In addition to this, α2,3-, α2,8-, and α2,9-sialic acids can be distinguishably detected on the basis of the structure of a glycan, such as whether or not a sialic acid is present at a non-reducing end.

Aspects

Those skilled in the art understand that the exemplary embodiments and modifications thereof described above are specific examples of the following aspects.

Item 1

A method for preparing an analysis sample according to one aspect is a method for preparing an analysis sample from a sample containing a glycan, the method comprising: performing esterification reaction that subjects at least a part of a sialic acid included in the glycan to esterification other than lactonization; and performing amidation reaction that converts an esterified form of a sialic acid modified through the esterification into an amidated form through contacting the sample with an amidation reaction solution containing at least one compound selected from the group consisting of ammonia, amines, hydrazine, hydrazine derivatives, and hydroxyamine, and salts thereof to be reacted with the sialic acid modified through the esterification. This method enables modification of sialic acid through a novel mechanism for analysis of a sialic acid included in a glycan.

Item 2

A method for preparing an analysis sample according to another aspect is the method for preparing an analysis sample according to the aspect of item 1, the method comprising: performing the esterification reaction through contacting the sample with an esterification reaction solution, wherein the esterification reaction solution contains at least one of an alcohol and an esterifying agent. This method enables more reliable esterification of a sialic acid included in a glycan.

Item 3

A method for preparing an analysis sample according to another aspect is the method for preparing an analysis sample according to the aspect of item 2, wherein the esterification reaction solution contains the esterifying agent; and the esterifying agent is a triazene derivative. This method enables efficient esterification of a sialic acid included in a glycan.

Item 4

A method for preparing an analysis sample according to another aspect is the method for preparing an analysis sample according to the aspect of item 2 or 3, wherein the amidation reaction is performed only through contacting the sample with the amidation reaction solution after an operation to remove the esterification reaction solution from the sample. This method enables preparation of an analysis sample in a simple manner.

Item 5

A method for preparing an analysis sample according to another aspect is the method for preparing an analysis sample according to the aspect of any one of items 2 to 4, wherein the amidation reaction solution is free of a dehydration condensation agent. This method enables preparation of an amidation reaction solution in a simpler manner.

Item 6

A method for preparing an analysis sample according to another aspect is the method for preparing an analysis sample according to the aspect of any one of items 1 to 5, wherein an operation of reacting the sample with a dehydration condensation agent is not performed after contacting the sample with the amidation reaction solution. This method enables reduction of the number of steps in preparing an analysis sample, making the preparation simpler.

Item 7

A method for preparing an analysis sample according to another aspect is the method for preparing an analysis sample according to the aspect of any one of items 1 to 6, wherein a time during which the sample is in contact with the amidation reaction solution to perform the amidation reaction is shorter than 30 minutes. This method enables efficient preparation of an analysis sample in a shorter time.

Item 8

A method for preparing an analysis sample according to another aspect is the method for preparing an analysis sample according to the aspect of any one of items 1 to 7, wherein an operation to cleave a lactone structure formed through the esterification reaction is not performed before the amidation reaction. This method enables more reliable amidation of α2,3-sialic acid, α2,8-sialic acid, α2,9-sialic acid, and so on, which readily undergo lactone formation.

Item 9

A method for preparing an analysis sample according to another aspect is the method for preparing an analysis sample according to the aspect of any one of items 1 to 8, wherein the compound is a primary amine. This method enables more reliable modification of a sialic acid based on the reactivity of the compound.

Item 10

A method for preparing an analysis sample according to another aspect is the method for preparing an analysis sample according to the aspect of item 9, wherein one or no carbon atom is directly bonding to a carbon atom bonding to an amino group of the primary amine. This method enables further reliable modification of a sialic acid based on the reactivity of the compound.

Item 11

A method for preparing an analysis sample according to another aspect is the method for preparing an analysis sample according to the aspect of any one of items 1 to 10, wherein the compound includes an alkyl group. This method enables furthermore reliable modification of a sialic acid based on the reactivity of the compound.

Item 12

A method for preparing an analysis sample according to another aspect is the method for preparing an analysis sample according to the aspect of any one of items 1 to 10, wherein the pH of the amidation reaction solution is 7.7 or higher. In this method, amidation reaction is more likely to occur under basic conditions, and a sialic acid can be more reliably modified.

Item 13

A method for preparing an analysis sample according to another aspect is the method for preparing an analysis sample according to the aspect of any one of items 2 to 5, wherein at least a part of a sialic acid not modified through the esterification is lactonized through contacting the sample with the esterification reaction solution; and a lactone structure of the sialic acid modified through the lactonization is converted into an amidated form through contacting the sample with the amidation reaction solution. With this method, a sialic acid can be amidated even if lactonization occurred through the esterification reaction in the same manner as when esterification occurred.

Item 14

A method for preparing an analysis sample according to another aspect is the method for preparing an analysis sample according to the aspect of any one of items 1 to 13, wherein at least one sialic acid selected from the group consisting of $\alpha 2,3$-sialic acid, $\alpha 2,8$-sialic acid, and $\alpha 2,9$-sialic acid is amidated in the amidation reaction. In this method, $\alpha 2,3$-sialic acid, $\alpha 2,8$-sialic acid, or $\alpha 2,9$-sialic acid can be amidated through a novel mechanism.

Item 15

A method for preparing an analysis sample according to another aspect is the method for preparing an analysis sample according to the aspect of any one of items 1 to 14, wherein a concentration of the compound in the amidation reaction solution for the amidation reaction is controlled so as not to cause conversion of an esterified form of $\alpha 2,6$-sialic acid modified through the esterification into the amidated form. With this method, $\alpha 2,3$-sialic acid, $\alpha 2,8$-sialic acid, and $\alpha 2,9$-sialic acid can be analyzed distinguishably from $\alpha 2,6$-sialic acid.

Item 16

A method for preparing an analysis sample according to another aspect is the method for preparing an analysis sample according to the aspect of any one of items 1 to 15, wherein at least one of the esterification reaction and the amidation reaction is performed in such a state that the sample is bonding to or adsorbed on a solid phase carrier. This method simplifies operations including purification, and enables efficient preparation of an analysis sample.

Item 17

A method for preparing an analysis sample according to another aspect is the method for preparing an analysis sample according to the aspect of any one of items 1 to 16, wherein a solvent of the amidation reaction solution contains an organic solvent. This method prevents amidation of $\alpha 2,6$-sialic acid, and enables more precise linkage-specific analysis. In addition, structure-specific amidation of sialic acids can be achieved.

Item 18

A method for preparing an analysis sample according to another aspect is the method for preparing an analysis sample according to the aspect of item 17, wherein the organic solvent is acetonitrile. This method enables more reliable structure-specific amidation of sialic acids.

Item 19

A method for preparing an analysis sample according to another aspect is the method for preparing an analysis sample according to the aspect of item 17 or 18, wherein at least one sialic acid selected from the group consisting of $\alpha 2,3$-sialic acid, $\alpha 2,8$-sialic acid, and $\alpha 2,9$-sialic acid in the amidation reaction is amidated on the basis of a position of the at least one sialic acid in the glycan or a structure of the glycan. This method enables acquisition of information on a position of a sialic acid in a glycan or the structure of a glycan, and analysis using such information.

Item 20

A method for preparing an analysis sample according to another aspect is the method for preparing an analysis sample according to the aspect of item 19, the method further comprising: performing the amidation reaction by using an amidation reaction solution containing the organic solvent, and then performing amidation of a sialic acid not amidated through the amidation reaction through contacting an amidation reaction solution containing an aqueous solvent with the sample that has been subjected to the amidation reaction. With this method, three or more sialic acids of different linkage types or at different positions in a glycan can be distinguishably detected.

Item 21

A method for preparing an analysis sample according to another aspect is the method for preparing an analysis sample according to the aspect of any one of items 1 to 20, the method comprising: preparing a first analysis sample from the sample after being subjected to the amidation reaction; and preparing a second analysis sample from the sample after being subjected to the esterification reaction and before being subjected to the amidation reaction. This method enables more detailed analysis of a glycan through comparison between analysis of the first analysis sample and analysis of the second analysis sample.

Item 22

A method for preparing an analysis sample according to one aspect comprises: preparing a sample by using the method for preparing an analysis sample according to the aspect of any one of items 1 to 20; and performing analysis of the sample prepared. This method enables analysis of a sialic acid included in a glycan with use of modification through a novel mechanism.

Item 23

A method for preparing an analysis sample according to another aspect comprises: preparing the first analysis sample and the second analysis sample by using the method for preparing an analysis sample according to the aspect of item 21; performing analysis of the first analysis sample and the second analysis sample prepared; and performing analysis of the first analysis sample and the second analysis sample prepared; and performing data analysis of a glycan contained in the sample on the basis of a difference between data acquired in the analysis for the first analysis sample and data acquired in the analysis for the second analysis sample. This method enables more detailed analysis of a glycan through comparison between analysis of the first analysis sample and analysis of the second analysis sample.

Item 24

A method for preparing an analysis sample according to another aspect is the method for preparing an analysis sample according to the aspect of item 22 or 23, wherein the analysis is performed through at least one of mass spectrometry and chromatography. With this method, even a sample with various substances can be analyzed with the substances separated.

Item 25

A kit for preparing an analysis sample according to one aspect is used for the method for preparing an analysis sample according to the aspect of any one of items 1 to 20. With the kit, an analysis sample can be efficiently prepared.

The present invention is never limited to the contents of the above embodiments. Other modes contemplated from the scope of the technical idea of the present invention are also included in the scope of the present invention.

EXAMPLES

Now, examples according to the embodiments will be presented. However, the present invention is not limited to Examples below. Hereinafter, "%" denotes vol/vol %, unless otherwise stated.

Examples 1 to 4

In each of Examples 1 to 4, esterification reaction and amidation reaction were performed for an N-glycan bonded to a carrier, and the resulting glycan sample was analyzed through mass spectrometry.

Production of Glycan Evaluation Sample Including α2,3-Sialic Acid

Procedures according to 1 to 3 below were performed in the numerical order to produce the glycan called A2 glycan (33A2) including two α2,3-sialic acids. From α2,3-sialylglycopeptide (SGP) (FUSHIMI Pharmaceutical Co., Ltd.), A2 glycan (33A2) was released with PNGase F. The released glycan was subjected to desalting treatment with a Stage Tip Carbon. The Stage Tip Carbon is a carbon column prepared by cutting an Empore Disk-Carbon (produced by 3M Company) into pieces having a diameter of approximately 1 mm and packing a 200 µL tip with the pieces.

1. A solution containing α2,3-SGP at a concentration of 1 nmol/µL was aliquoted into 20 µL portions in tubes, and 10 µL of 0.25 U/µL PNGase F (Sigma-Aldrich Co. LLC) was added to each tube (2.5 U/tube).
2. Soft tapping and centrifugation were performed, and incubation was performed at 37° C. overnight (o/n).
3. On the next day, the glycan was desalted with a Stage Tip Carbon.

Production of Glycan Evaluation Sample Including α2,6-Sialic Acid

The glycan A2GN1 (Tokyo Chemical Industry Co., Ltd.), which includes α2,6-sialic acid, was redissolved in water and mixed, and the resultant was used as a glycan evaluation sample.

Esterification Reaction and Amidation Reaction

Procedures according to 1 to 8 below were performed in the numerical order to subject the glycan evaluation sample produced to esterification reaction and amidation reaction. Which of 1-methyl-3-p-tolyltriazene (MTT) and 1-ethyl-3-p-tolyltriazene (ETT) was used in the esterification reaction, and amidation reactants used in the amidation reaction will be described in Results for each Example.

1. The glycan evaluation sample produced was bonded to hydrazide beads (BlotGlyco; Sumitomo Bakelite Co., Ltd.). The bonding performed was in accordance with a protocol for BlotGlyco.
2. To the beads, 100 µL of a solution containing 500 mM MTT or ETT in a solvent of DMSO was added, and reacted at 60° C. for 1 hour (esterification reaction).
3. The beads were washed three times with 200 µL of methanol.
4. To the beads, 100 µL of an amidation reaction solution was added, the resultant was stiffed, and the amidation reaction solution was then removed through centrifugation.
5. The beads were washed three times with 200 µL of methanol.
6. The glycan sample was released from the beads. The release performed was in accordance with a protocol for Blotglyco.
7. The glycan sample released was subjected to evaporation to dryness through centrifugal concentration under reduced pressure.
8. The glycan was desalted with a Stage Tip Carbon.

Mass Spectrometry

The glycan after being desalted and subjected to evaporation to dryness was redissolved in 20 µL of water. To a 700-µm µFocus plate (Hudson Surface Technology, Inc.), 0.5 µL of the solution resulting from the redissolution was added dropwise. A matrix solution containing 5 mg/mL 2,5-dihydroxybenzoic acid (DHB) dissolved in 50% acetonitrile (ACN) (with 5 mM NaCl) was added as a matrix, the resultant was dried in air flow at normal temperature/normal pressure, and 0.2 µL of ethanol was then added for recrystallization to afford a mass spectrometry sample. Thereafter, measurement was performed with a MALDI-quadrupole ion trap/time-of-flight mass spectrometer (MALDI-QIT-TOF-MS) (AXIMA-Resonance, Shimadzu/Kratos) in the positive ion mode.

Results

Figure 6:
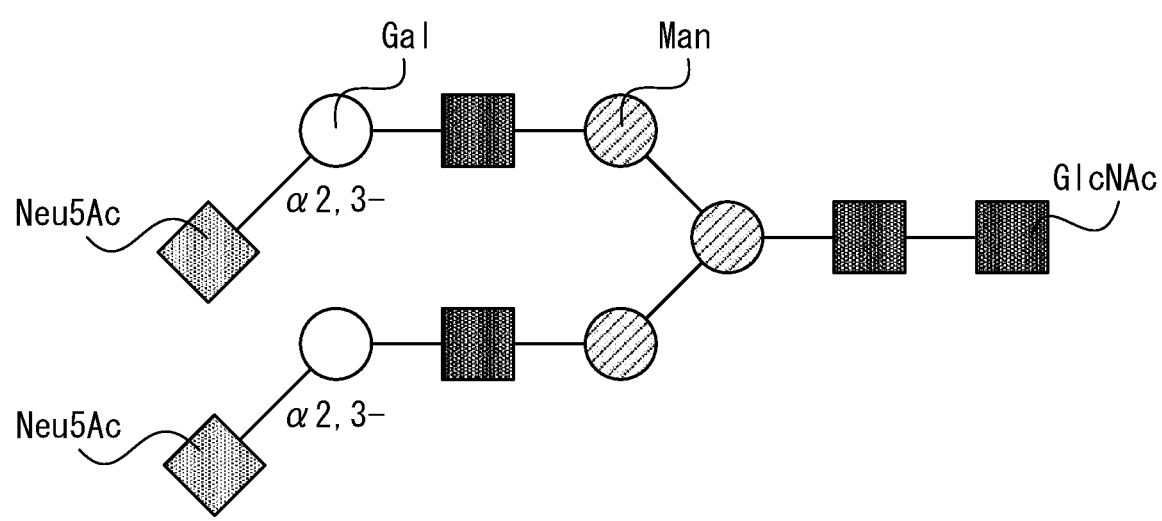
FIG. 6 shows a conceptual diagram illustrating the structure of a glycan used in Examples.

FIG. 6 shows a conceptual diagram illustrating the structure of a glycan sample including α2,3-sialic acid (hereinafter, referred to as the α2,3-glycan sample) used in these Examples. The α2,3-glycan sample includes a basic structure consisting of N-acetyl-D-glucosamine (GlcNAc) and mannose (Man), and two side chains. To each of the two side chains, GlcNAc, galactose (Gal), and sialic acid (Neu5Ac) are bonded.

A glycan sample including α2,6-sialic acid (hereinafter, referred to as the α2,6-glycan sample) used in these Examples is the glycan A2GN1 illustrated in FIG. 4C. The α2,6-glycan sample differs from the α2,3-glycan sample in the linkage type of sialic acid, and they are different in that the number of GlcNAc moieties in the α2,6-glycan sample is one less than that in the α2,3-glycan sample.

Example 1

Figure 7:
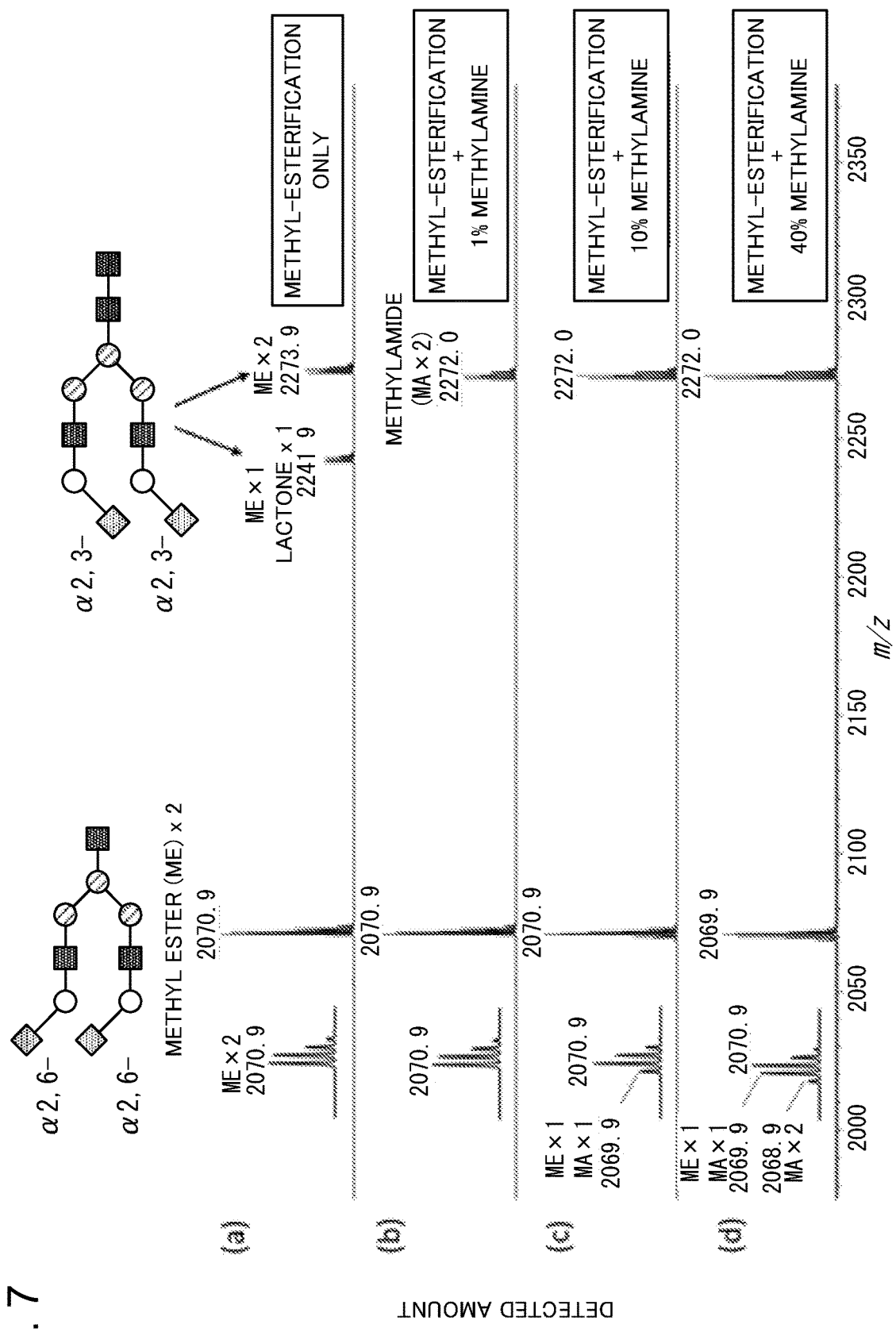
FIG. 7 shows (a) a mass spectrum of an analysis sample prepared in such a manner that methyl-esterification reaction was performed and amidation reaction was not performed, and mass spectra of analysis samples prepared in such a manner that methyl-esterification reaction was performed and amidation reaction was then performed by using (b) 1%, (c) 10%, or (d) 40% methylamine aqueous solution.

Mass spectrum (a) in FIG. 7 is a mass spectrum of a sample obtained in such a manner that modification reaction through methyl-esterification of sialic acids was performed for a glycan bonded to a solid phase carrier, and the glycan was released without performing amidation reaction. In the mass spectrum, the horizontal axis represents m/z of detected ions and the vertical axis represents intensity of detection signals for detected ions, and the same is applied to the subsequent figures. The peak at m/z 2070.9 corresponds to a peak for the α2,6-glycan sample in which the two sialic acids in the glycan were both methyl-esterified. For the α2,3-glycan sample, on the other hand, two peaks, specifically, a peak for a product in which the two sialic acids were methyl-esterified (m/z 2273.9) and a peak for a product in which one of the two sialic acids was methyl-esterified and the other was lactonized (m/z 2241.9) were observed.

Mass spectra (b), (c), and (d) in FIG. 7 are mass spectra of samples obtained in such a manner that modification reaction through methyl-esterification of sialic acids was performed for a glycan bonded to a solid phase carrier, and amidation reaction was then performed by using (b) 1%, (c) 10%, or (d) 40% methylamine solution on wt/vol % basis. In the samples subjected to methyl-esterification reaction followed by amidation reaction, not only lactonized α2,3-sialic acid was converted into methylamide, but also methyl-esterified α2,3-sialic acid was converted into methylamide. Surprisingly, α2,6-sialic acid, in spite of having the same ester structure, was almost free from amidation, and remained methyl ester. When being treated with thick methylamine with a concentration of 10% or more, even α2,6-sialic acid appeared to only slightly undergo methylamidation; however, the reaction rate was small, in contrast to α2,3-sialic acid, which is extremely efficiently converted into amide. Thus, α2,6-sialic acid and α2,3-sialic acid can be distinguished from each other to a sufficient degree. This Example demonstrates that the amidation reaction solution in the above-described embodiment enables selective amidation of ester formed from α2,3-sialic acid, and that this technique is effective for identification of the linkage type of sialic acid.

Example 2

Figure 8:
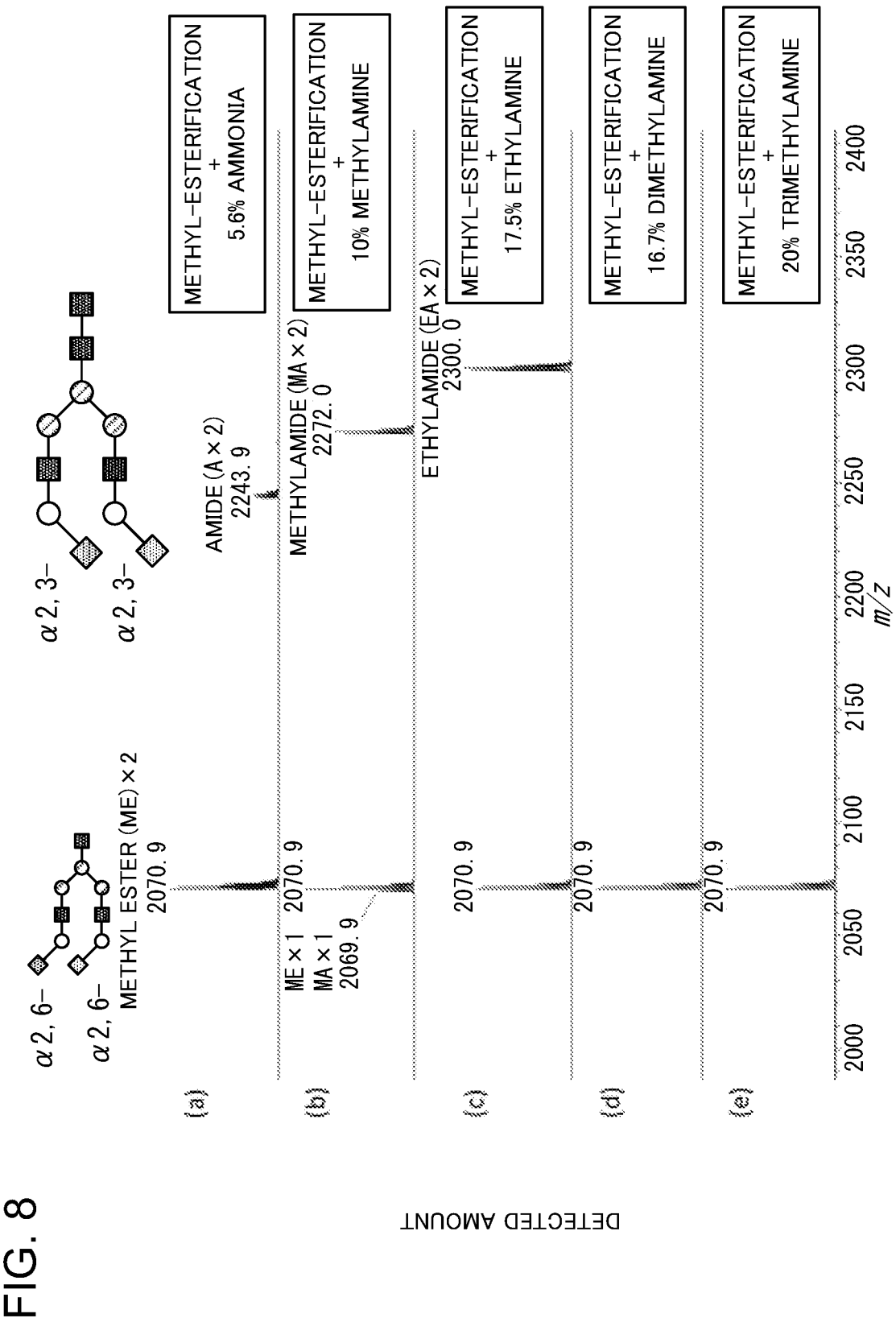
FIG. 8 shows mass spectra of analysis samples prepared in such a manner that methyl-esterification reaction was performed and amidation reaction was then performed by using (a) 5.6% ammonia water, (b) 10% methylamine solution, (c) 17.5% ethylamine solution, (d) 16.7% dimethylamine solution, or (e) 20% trimethylamine solution.

FIG. 8 shows mass spectra of samples obtained in such a manner that, for a glycan bonded to a solid phase carrier, modification reaction through methyl-esterification of sialic acids was performed and amidation reaction was then performed by using (a) 5.6% ammonia water, (b) 10% methylamine solution, (c) 17.5% ethylamine solution, (d) 16.7% dimethylamine solution, or (e) 20% trimethylamine solution on wt/vol % basis. When (a) ammonia was used, the peaks at m/z 2273.9 and at m/z 2241.9 shown in (a) of FIG. 7 were not detected, and peaks converged to a peak at m/z 2243.9 corresponding to a glycan in which the two sialic acids were amidated. Accordingly, it is understood that α2,3-sialic acid was structure-specifically amidated. (b) shows results similar to those in (b) of FIG. 7. It is understood that even when (c) ethylamine was used, linkage-specific ethylamidation was achieved without any problem (m/z 2300.0). When (d) dimethylamine or (e) trimethylamine was used, on the other hand, the peak corresponding to the glycan including α2,3-sialic acid disappeared. Because these are amines that are less likely to cause aminolysis of lactones (see NPTL 2), it can be inferred that hydrolysis was promoted and as a result the original carboxylic acid (—COOH) structure was recovered, leading to lowered ionization efficiency, which disabled detection in the positive ion mode.

Example 3

Figure 9:
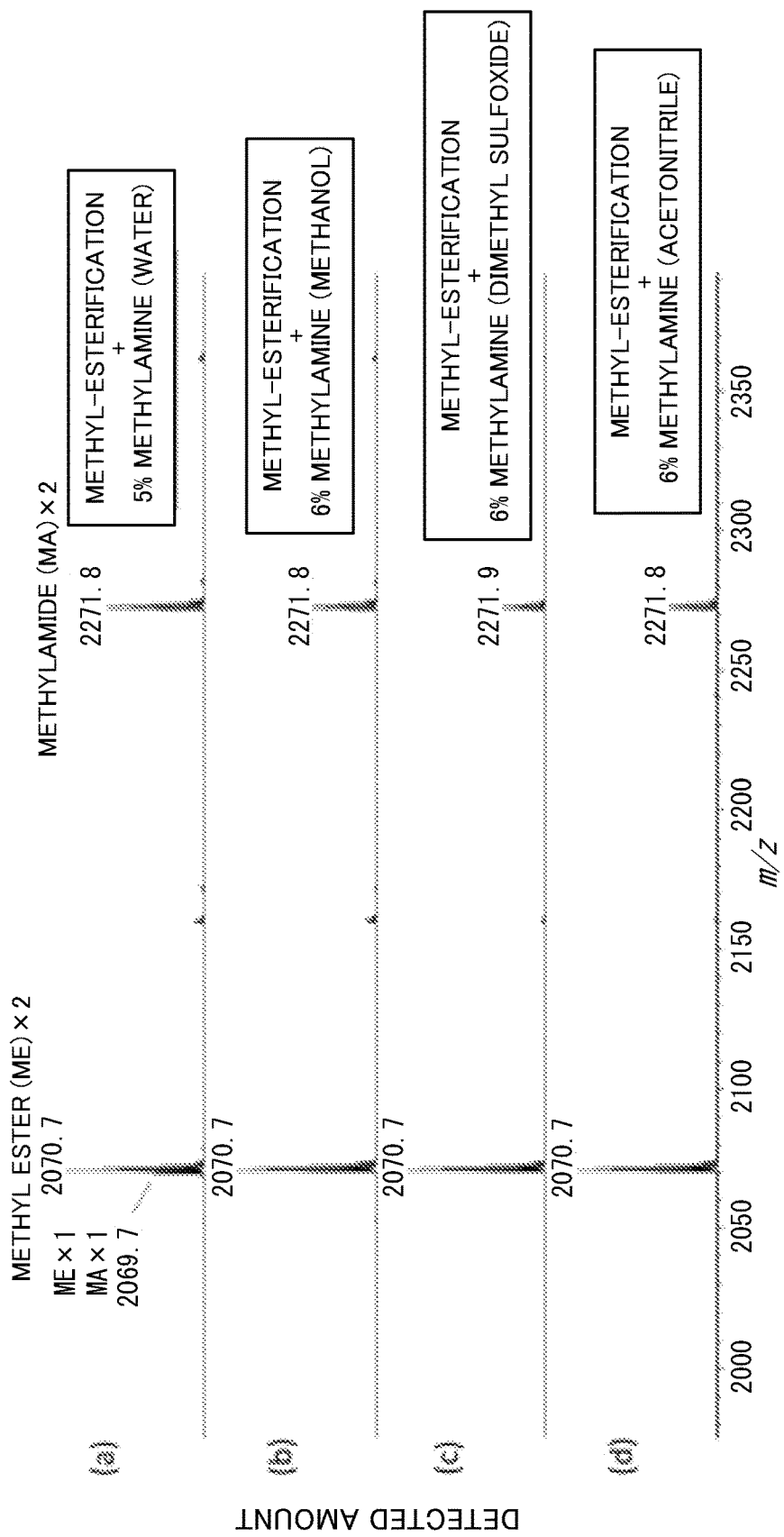
FIG. 9 shows (a) a mass spectrum of an analysis sample prepared in such a manner that methyl-esterification reaction was performed and amidation reaction was then performed by using 5% methylamine aqueous solution, and mass spectra of analysis samples prepared in such a manner that methyl-esterification reaction was performed and amidation reaction was then performed by using 6% methylamine solution with a solvent of (b) methanol, (c) dimethyl sulfoxide, or (d) acetonitrile.

FIG. 9 shows mass spectra of samples obtained in such a manner that, for a glycan bonded to a solid phase carrier, modification reaction through methyl-esterification of sialic acids was performed and amidation reaction was then performed by using 5% or 6% (wt/vol %) methylamine solution with a solvent of (a) water, (b) methanol, (c) dimethyl sulfoxide, or (d) acetonitrile. It was demonstrated that, even with organic solvents, amidation specific to α2,3-sialic acid proceeded without any problem. Amidation of α2,6-sialic acid ester was more suppressed under organic solvent conditions than with a solvent of water.

Example 4

In FIG. 10, (a) in the top shows a mass spectrum of a sample obtained in such a manner that modification reaction through methyl-esterification of sialic acids was performed by using MTT, and ethylamidation reaction was then performed by using 17.5% (wt/vol %) ethylamine solution. In FIG. 10, (b) in the bottom shows a mass spectrum of a sample obtained in such a manner that modification reaction through ethyl-esterification of sialic acids was performed by using ETT, and methylamidation reaction was then performed by using 10% (wt/vol %) methylamine solution. It is understood that even when combination of ester and amine was changed, esterified α2,3-sialic acid was selectively converted into amide without any problem.

Example 5

In Example 5, esterification reaction and amidation reaction were performed for a glycolipid-type glycan bonded to a carrier, and the resulting glycan sample was analyzed through mass spectrometry.
Production of Glycan Evaluation Sample The human disialogangliosides GD1a and GD1b (HyTest Ltd.), which are glycosphingolipids, were used as samples. Each of the glycolipids was dissolved in 45 μL of 50 mM sodium acetate buffer (pH 5.5) containing 0.2% Triton x100, and left to stand with warming at 60° C. for 20 minutes, and 5 μL of endoglycoceramidase I (purified from actinomycete with reference to the following literature; Ishibashi Y, Nakasone T, Kiyohara M, Horibata Y, Sakaguchi K, Hijikata A, Ichinose S, Omori A, Yasui Y, Imamura A, Ishida H, Kiso M, Okino N, and I to M. "A novel endoglycoceramidase hydrolyzes oligogalactosylceramides to produce galactooligosaccharides and ceramides," Journal of Biological Chemistry, 2007, Volume 282, pp. 11386-11396) was added thereto, and glycan release reaction was performed at 37° C. for 16 hours.
Esterification Reaction and Amidation Reaction Procedures according to 1 to 7 below were performed in the numerical order to subject the glycan evaluation sample produced to esterification reaction and amidation reaction.
1. The glycan evaluation sample produced was bonded to a solid phase carrier (BlotGlyco). The bonding performed was in accordance with a protocol for BlotGlyco.
2. To the beads, a solution containing 500 mM MTT in a solvent of DMSO was added to perform esterification reaction.
3. The solid phase carrier was washed three times with 200 μL of methanol.
4. Amidation reaction was performed by washing the solid phase carrier three times with 200 μL of methylamine solution.
5. The solid phase carrier was washed three times with 200 μL of water.

6. In accordance with a protocol for BlotGlyco, the reducing end of the glycan was reacted with aoWR, a high-sensitivity label for MALDI.
7. An excessive portion of the reagents was removed from the sample by using a HILIC plate (Waters Corporation).

Mass Spectrometry

Measurement was performed by using an Ultraflex II TOF/TOF-MS (Bruker) with a matrix of DHB in the positive ion mode.

Results

The structures of the glycans GD1a and GD1b used in this Example are shown in FIGS. 4A and 4B, respectively.

Figure 11:
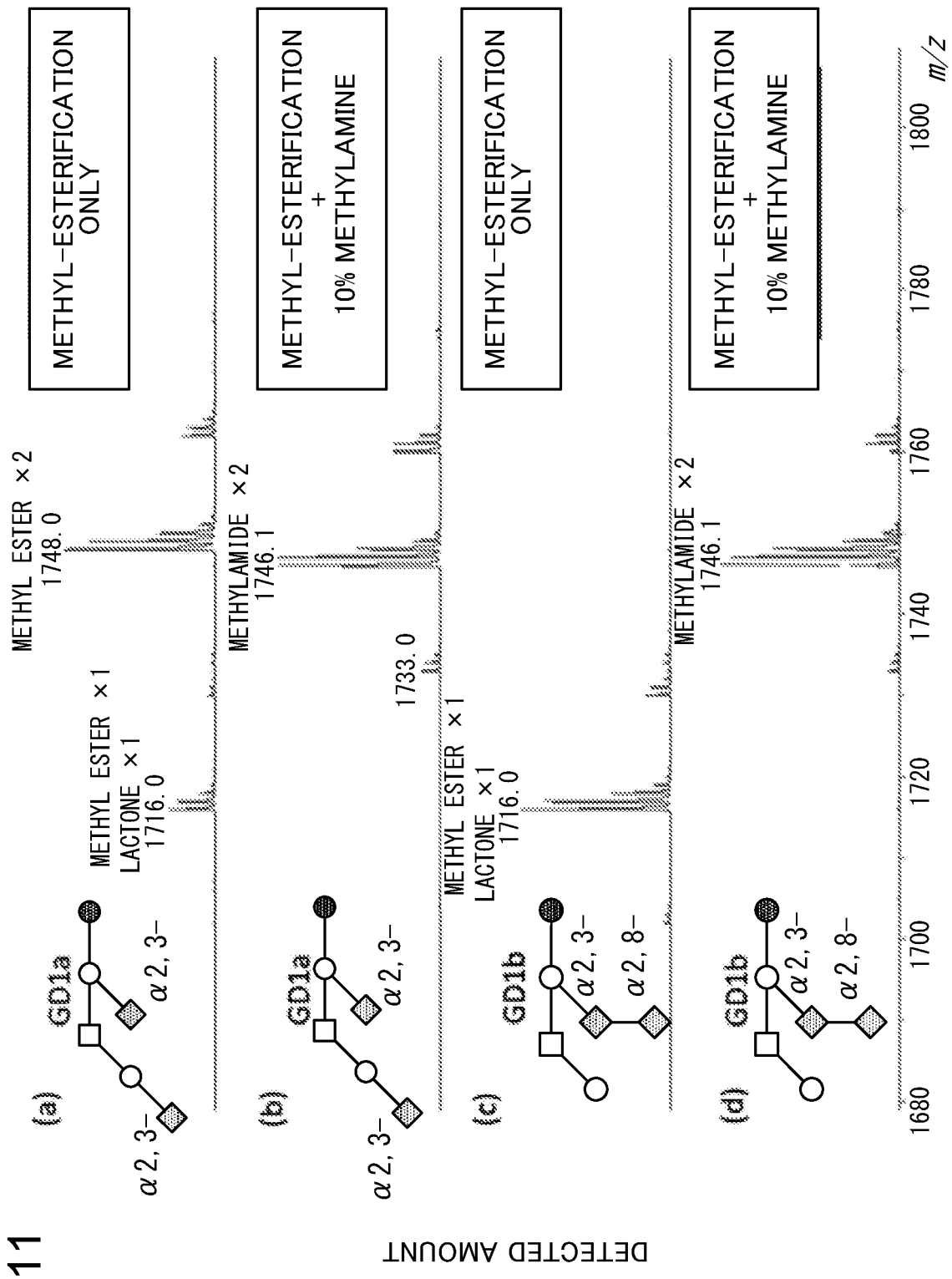
FIG. 11 shows (a) a mass spectrum of an analysis sample prepared in such a manner that, for a sample containing the glycan GD1a, methyl-esterification reaction was performed and amidation reaction was not performed, (b) a mass spectrum of an analysis sample prepared in such a manner that, for a sample containing the glycan GD1a, methyl-esterification reaction was performed and amidation reaction was then performed by using 10% methylamine solution, (c) a mass spectrum of an analysis sample prepared in such a manner that, for a sample containing the glycan GD1b, methyl-esterification reaction was performed and amidation reaction was not performed, and (d) a mass spectrum of an analysis sample prepared in such a manner that, for a sample containing the glycan GD1b, methyl-esterification reaction was performed and amidation reaction was then performed by using 10% methylamine solution.

FIG. 11 shows mass spectra of samples obtained in such a manner that, for the glycan GD1a for the sample, modification reaction through methyl-esterification was performed and (a) amidation was not performed thereafter or (b) amidation was then performed by using 10% (wt/vol %) methylamine solution, and mass spectra of samples obtained in such a manner that, for the glycan GD1b for the sample, modification reaction through methyl-esterification was performed and (c) amidation was not performed thereafter or (d) amidation was then performed by using 10% (wt/vol %) methylamine solution.

For GD1a, when methyl-esterification with MTT was performed and amidation was not performed, a peak corresponding to the case that two α2,3-sialic acids were methyl-esterified (m/z 1748) and a peak corresponding to the case that one of the two α2,3-sialic acids was lactonized (m/z 1716) were observed. When amidation reaction with methylamine solution was performed after methyl-esterification, products converged to a methylamidated form.

For GD1b, when methyl-esterification with MTT was performed and amidation was not performed, a peak for a glycan to which methyl-esterification and lactonization were caused (m/z 1716) was primarily observed. When amidation reaction with methylamine solution was performed after methyl-esterification, products converged to a methylamidated form. This suggests that conversion of sialic acid from ester to amide (ester-to-amide conversion) specific to the linkage type of sialic acid in the above-described embodiment is effective not only for α2,3-sialic acid but also for α2,8-sialic acid.

Example 6

In Examples described above, amidation reaction was performed for glycans bonded to a solid phase carrier. In this Example, amidation reaction was performed for a sample of a standard serum-derived N-glycan adsorbed on a solid phase carrier, and the resulting glycan sample was analyzed through mass spectrometry.

Production of Glycan Evaluation Sample

Commercially available serum was reductively alkylated, and then subjected to tryptic digestion and release of a glycan with PNGase F to prepare a N-glycan.

Esterification Reaction

Procedures according to 1 to 5 below were performed in the numerical order to subject the serum glycoprotein-derived N-glycan to esterification reaction, and the reducing end was labeled with aoWR.
1. The N-glycan prepared was bonded to beads (BlotGlyco). The bonding performed was in accordance with a protocol for BlotGlyco.
2. To the beads, 100 μL of a 500 mM solution of MTT dissolved in DMSO was added, and reacted at 60° C. for 1 hour.
3. The beads were washed three times with 200 μL of methanol.
4. The glycan was labeled with an aoWR reagent, and recovered.
5. The aoWR reagent was removed by using a HILIC plate (Waters Corporation).

Amidation Reaction

The human serum glycoprotein-derived N-glycan after the esterification reaction was diluted with 99% acetonitrile/1% acetic acid to adjust the concentration to 90% acetonitrile. Thereafter, a solution containing the glycan sample was applied to a HILIC plate (Waters Corporation), and the solution was passed through the carrier of the plate by vacuum suction from the back to allow the HILIC carrier to adsorb the glycan thereon. Then, acetonitrile containing 5 to 40% (wt/vol %) ethylamine to perform ester-to-amide conversion, as an amidation reaction solution, was added to the plate, and the amidation reaction solution was passed through the carrier of the plate by vacuum suction from the back. Thereafter, 95% acetonitrile/1% acetic acid was added to the plate, and the plate carrier was washed similarly by vacuum suction from the back. This operation was repeated three times. Finally, 5% acetonitrile/1% acetic acid was added to the plate to elute the glycan from the HILIC plate.

Mass Spectrometry

Measurement was performed by using an Ultraflex II TOF/TOF-MS (Bruker) with a matrix of DHB in the positive ion mode.

Results

Figure 12:
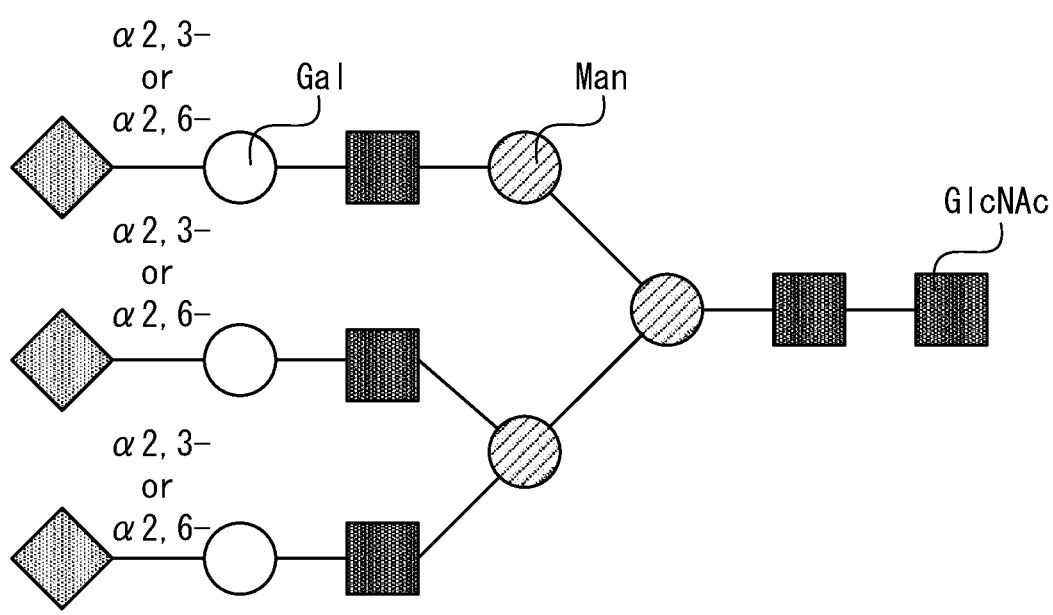
FIG. 12 shows a conceptual diagram illustrating the structure of a glycan used in Examples.

FIG. 12 shows a conceptual diagram illustrating an example of the structure of the human serum glycoprotein-derived N-glycan detected in this Example. The glycan sample illustrated in FIG. 12 includes a basic structure consisting of GlcNAc and Man and three side chains. To each of the three side chains, GlcNAc, Gal, and sialic acid (Neu5Ac) are bonded. The linkage type of each sialic acid is α2,3- or α2,6-. Such a glycan was detected also in Example 7 described later.

Figure 13:
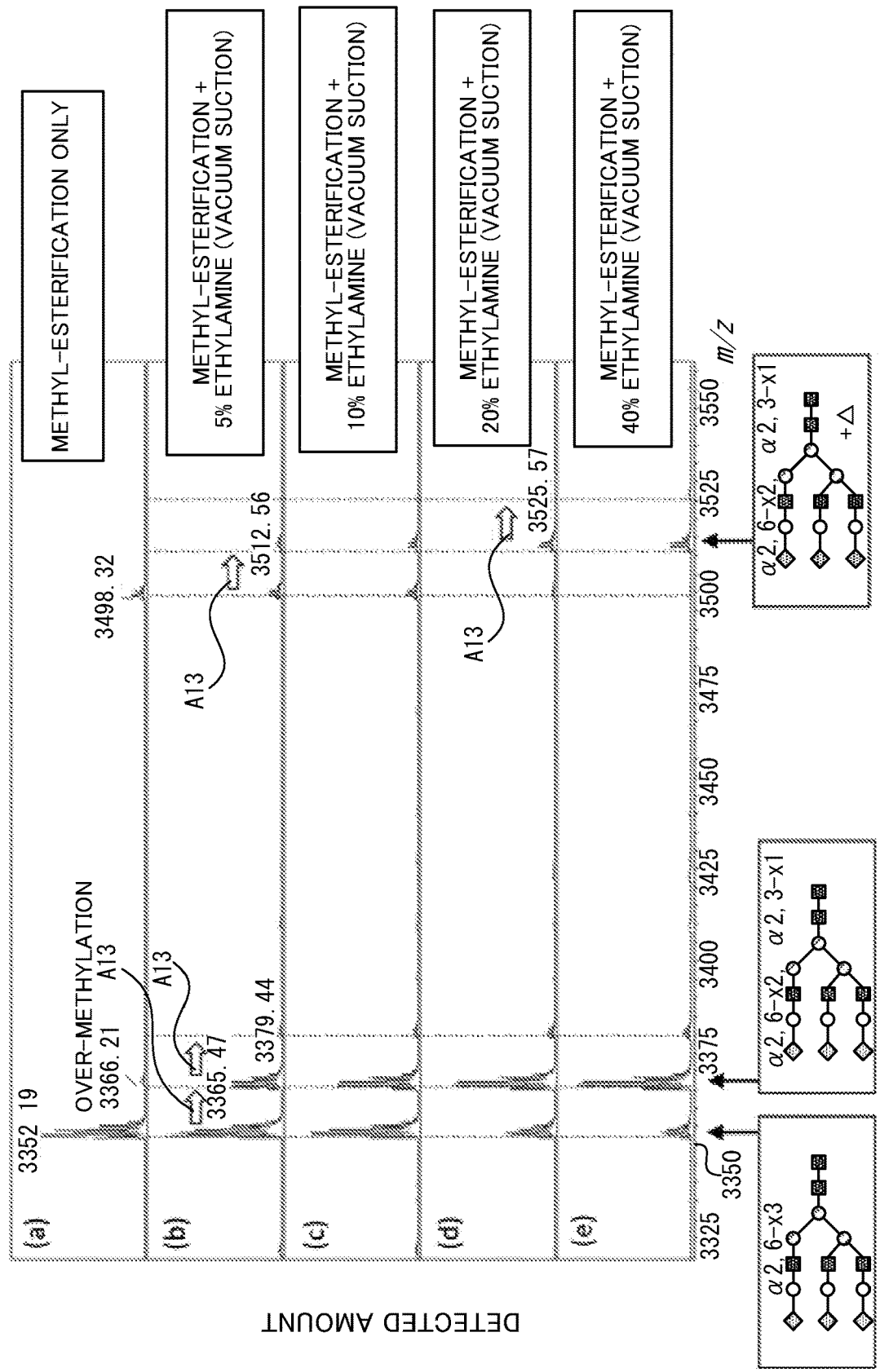
FIG. 13 shows (a) a mass spectrum of an analysis sample prepared in such a manner that, for a serum glycoprotein-derived N-glycan, methyl-esterification reaction was performed and amidation reaction was not performed, and mass spectra of analysis samples prepared in such a manner that, for a serum glycoprotein-derived N-glycan, methyl-esterification reaction was performed and amidation reaction was then performed by using (b) 5%, (c) 10%, (d) 20%, or (e) 40% ethylamine solution (purging by vacuum suction).

FIG. 13 shows parts of mass spectra acquired in this Example, the parts including peaks observed for the glycans illustrated in FIG. 12. Mass spectrum (a) is a mass spectrum of a sample obtained in such a manner that modification reaction through methyl-esterification was performed and amidation reaction was not performed thereafter. Mass spectra (b) to (e) are each a mass spectrum of a sample obtained in such a manner that modification reaction through methyl-esterification was performed and amidation reaction was then performed by using (b) 5%, (c) 10%, (d) 20%, or (e) 40% ethylamine solution on wt/vol % basis.

In spectrum (a), with methyl-esterification only, the trisialylated triantennary glycan in FIG. 12 was observed at m/z 3352.19, and a fucosylated trisialylated triantennary glycan, including fucose bonding to the trisialylated triantennary glycan (bonding of fucose to the glycan is schematically indicated by +A), was observed at m/z 3498.32. These are products in which all the sialic acids were methyl-esterified, and there is no distinction between α2,3- and α2,6-linkage types. A peak at m/z 3352.19+14 Da was additionally observed, and this corresponds to a peak derived from over-methylation, specifically, indiscriminate methylation of hydroxy groups.

Figure 14:
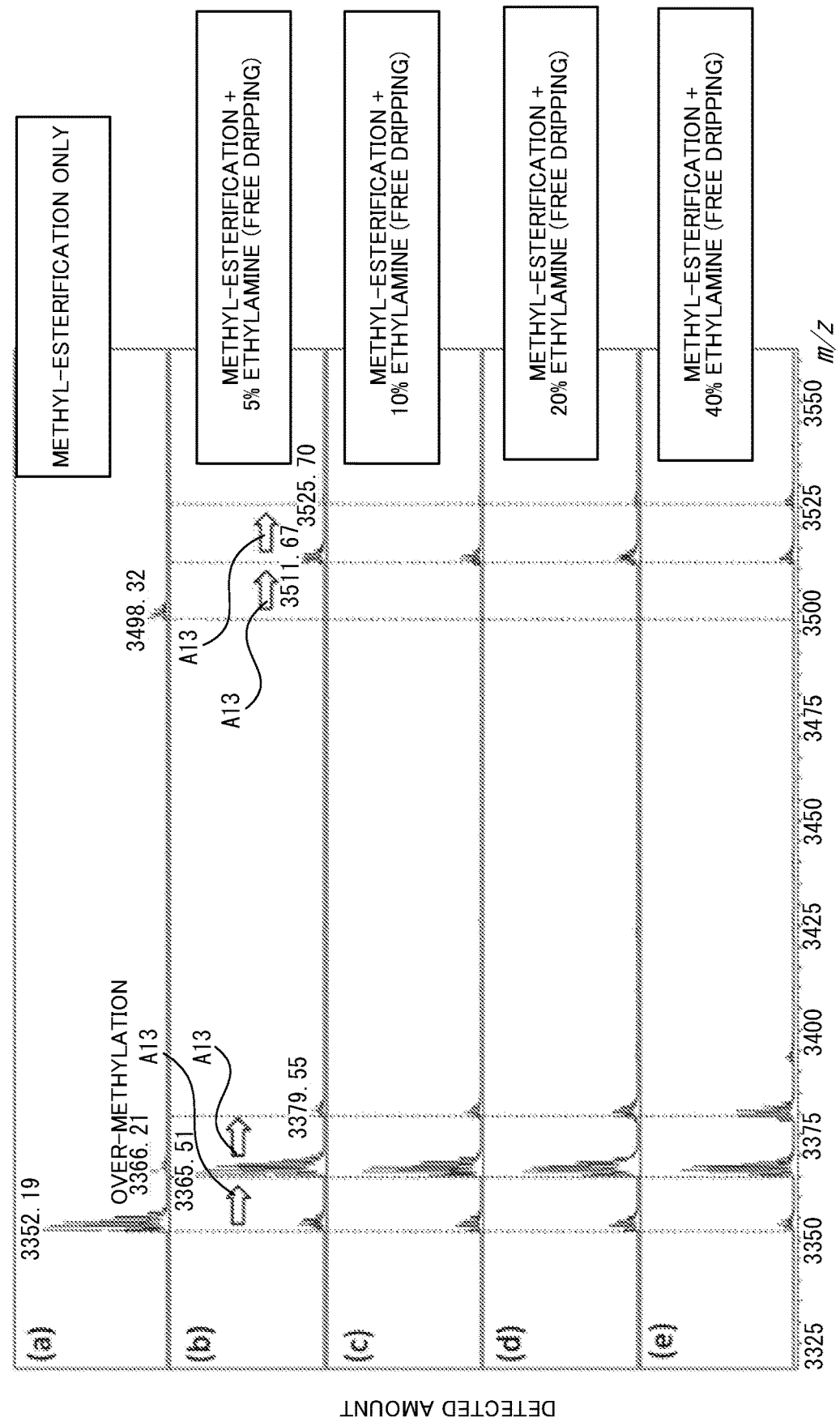
FIG. 14 shows (a) a mass spectrum of an analysis sample prepared in a manner such that, for a serum glycoprotein-derived N-glycan, methyl-esterification reaction was performed and amidation reaction was not performed, and mass spectra of analysis samples prepared in such a manner that, for a serum glycoprotein-derived N-glycan, methyl-esterification reaction was performed and amidation reaction was then performed by using (b) 5%, (c) 10%, (d) 20%, or (e) 40% ethylamine solution (purging by free dripping).
Figure 15:
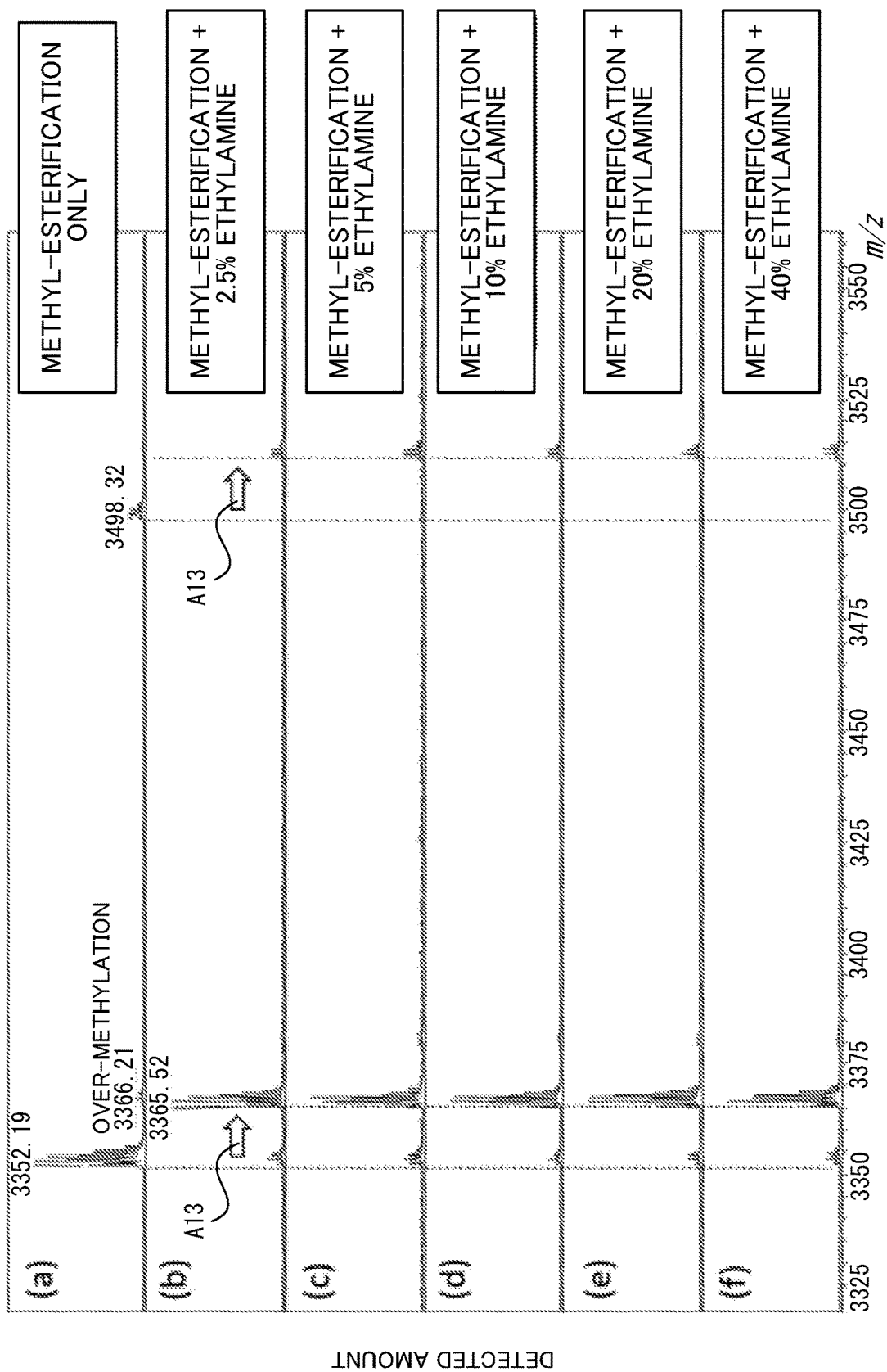
FIG. 15 shows a mass spectrum of an analysis sample prepared in such a manner that, for a serum glycoprotein-derived N-glycan, methyl-esterification reaction was performed and amidation reaction was not performed, and mass spectra of analysis samples prepared in such a manner that, for a serum glycoprotein-derived N-glycan, methyl-esterification reaction was performed and amidation reaction was then performed by using (b) 2.5%, (c) 5%, (d) 10%, (e) 20%, or (f) 40% ethylamine solution in a liquid phase.

When ester-to-amide conversion was performed with ethylamine on a HILIC plate ((b) to (e)), on the other hand, peak-shifting depending on the concentration was found. The trisialylated triantennary glycan subjected only to methyl-esterification (m/z 3352.19) is a mixture of a glycan in which all of the three sialic acids are of α2,6-linkage type and a glycan in which two sialic acids are of α2,6-linkage type and one sialic acid is of α2,3-linkage type, and the abundance ratio is approximately 1:9. Because α2,3-sialic acid is converted from methyl ester to ethylamide through ester-to-amide conversion, the intensity of the peak for a glycan having a mass increased by 13 Da increases. In FIGS. 13, 14, and 15, the change in m/z corresponding to 13 Da is schematically indicated by arrow A13. The fucosylated trisialylated triantennary glycan includes two α2,6-sialic acids and one α2,3-sialic acid with an abundance ratio of almost 100%, and hence the mass completely shifts by 13 Da by the occurrence of ester-to-amide conversion. Peaks further shifted by +13 Da (m/z 3379.44 and 3525.57) were additionally detected, and these are peaks derived from over-amidation, specifically, further conversion of a part of α2,6-sialic acid esters into ethylamide. In summary, it is understood from FIGS. 13(*b*) to 13(*d*) that ester-to-amide conversion occurred specifically to α2,3-sialic acid in a manner depending on the concentration of ethylamine used. This experimental result suggests that linkage-specific ester-to-amide conversion can be caused even in an adsorbed state on a HILIC plate.

FIG. 14 shows mass spectra of samples obtained through the same experiment as for FIG. 13, except that not vacuum suction from the back but free dripping was employed only in passing an amidation reaction solution. This successfully prolonged the reaction time from several seconds to 20 to 30 minutes. Thereby, ester-to-amide conversion was efficiently caused even with low-concentration amine.

Example 7

In this Example, amidation reaction was performed for a sample of a standard serum-derived N-glycan in a liquid phase, and the resulting glycan sample was analyzed through mass spectrometry. Production of a glycan evaluation sample and esterification reaction were performed under the same conditions as in Example 6.
Amidation Reaction The human serum glycoprotein-derived N-glycan prepared with the above method was aliquoted into tubes, 10-fold diluted with acetonitrile solution containing 2.5 to 40% (wt/vol %) ethylamine, and lightly mixed with a vortex mixer for amidation reaction. Thereafter, a solution containing the sample was applied to a HILIC plate (Waters Corporation), and the solution was passed through the carrier of the plate by vacuum suction from the back to allow the HILIC carrier to adsorb the glycan thereon. Then, 95% acetonitrile/1% acetic acid was added to the plate, and the plate carrier was washed similarly by vacuum suction from the back. This operation was repeated three times. Finally, 5% acetonitrile/1% acetic acid was added to the plate to elute the glycan from the HILIC plate.
Mass Spectrometry Measurement was performed by using a MALDI-QIT-TOF-MS (AXIMA-Resonance, Shimadzu/Kratos) with a matrix of DHB in the positive ion mode.

FIG. 15 shows parts of mass spectra acquired in this Example, the parts including peaks observed for the glycans illustrated in FIG. 12. Mass spectrum (a) is a mass spectrum of a sample obtained in such a manner that modification reaction through methyl-esterification was performed and amidation reaction was not performed thereafter. Mass spectra (b) to (f) are each a mass spectrum of a sample obtained in such a manner that modification reaction through methyl-esterification was performed and amidation reaction was then performed by using (b) 2.5%, (c) 5%, (d) 10%, (e) 20%, or (f) 40% ethylamine solution on wt/vol % basis.

Despite that the period from addition of ethylamine with different concentrations to the glycan sample followed by mixing to the initiation of purification with the HILIC plate was around 1 minute, it was successfully confirmed that ester-to-amide conversion was caused without any problem even when ethylamine at a concentration as low as around 2.5% was used. In addition, it is understood that amidation of α2,6-sialic acid ester was successfully suppressed even with high-concentration amine. While purification was performed with the HILIC carrier in this Example, ester-to-amide conversion was performed as liquid-phase reaction before adsorption on the HILIC carrier, and hence it was demonstrated that linkage-specific ester-to-amide conversion proceeds without any problem even in liquid-phase reaction.

Example 8

Figure 16:
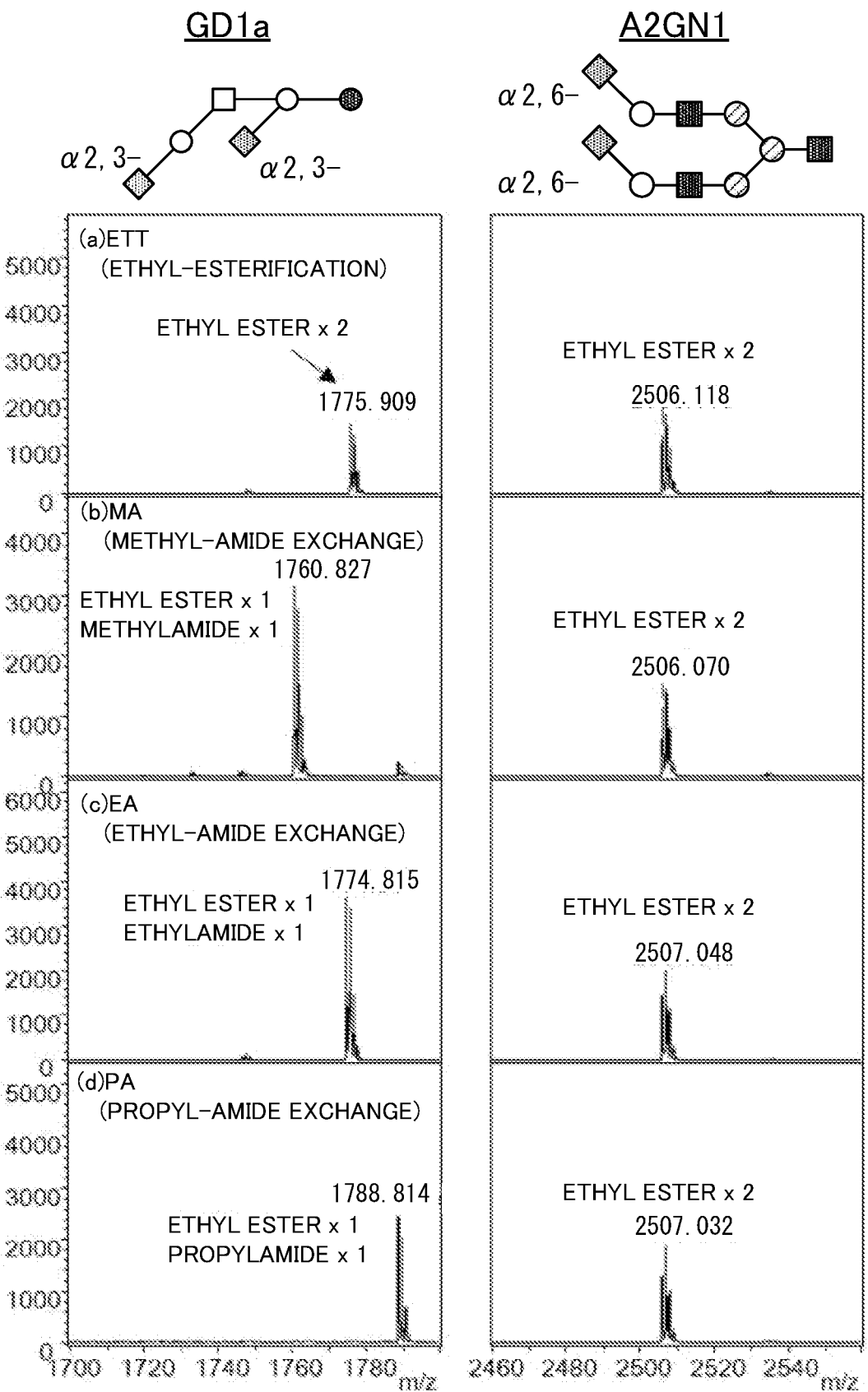
FIG. 16 shows (a) mass spectra of analysis samples prepared in such a manner that, for the glycan GD1a and the glycan A2GN1, ethyl-esterification reaction was performed and amidation reaction was not performed, and mass spectra of analysis samples prepared in such a manner that, for the glycan GD1a and the glycan A2GN1, ethyl-esterification reaction was performed and amidation reaction was then performed by using (b) methylamine solution, (c) ethylamine solution, or (d) propylamine solution with a solvent of acetonitrile.

In Example 8, ethyl-esterification reaction was performed for a GSL glycan, a glycan obtained from glycosphingolipid (GSL), bonded to a carrier, and amidation reaction was performed for the resulting glycan sample, which was analyzed through mass spectrometry.
Production of Glycan Sample Including α2,3-Sialic Acid and Esterification Reaction With the same method as in Example 5, glycans including two α2,3- or α2,8-sialic acids in total (GD1a, GD1b) were produced. Each of released glycans was bonded to a solid phase carrier through glycoblotting, subjected to ethyl-esterification with 1-ethyl-3-p-tolyltriazene (ETT), and recovered as an aoWR-labeled glycan (100 μL). A sample was similarly produced for the glycan A2GN1 in the same manner as in Example 1, and subjected to esterification reaction as described above in this Example.
Amidation Reaction and Mass Spectrometry Mixed together were 25 μL of the resulting aoWR-labeled glycan solution and 250 μL of amine solution (concentration: 1 mol/L, solvent:acetonitrile), and an excessive portion of the reagents was removed from the sample with a HILIC plate (Waters Corporation). Measurement was performed by using an Ultraflex II TOF/TOF-MS (Bruker) with a matrix of DHB in the positive ion mode. The glycan A2GN1 was also subjected to amidation reaction and mass spectrometry in the same manner.
Results FIG. 16 shows mass spectra of samples obtained in such a manner that, for the glycans GD1a and A2GN1 for the samples, modification reaction through ethyl-esterification was performed, and (a) amidation reaction was not performed thereafter, or (b, c, d) amidation reaction was then performed with acetonitrile solution containing 1 M (M denotes mol/L) methylamine, ethylamine, or propylamine. For GD1a, when ethyl-esterification with ETT was performed and amidation was not performed, a peak corresponding to the case that two α2,3-sialic acids were methyl-esterified (m/z 1776) was detected. In the subsequent figures, an arrow shown in a mass spectrum associates a peak with a modified form of a product. When amidation reaction with methylamine solution was performed after methyl-esterification, products converged to a product in which only one sialic acid was methylamidated (m/z 1761). When ethylamine or propylamine solution was used, similarly, products converged to a product in which only one sialic acid was amidated (m/z 1775, 1789).

Figure 17:
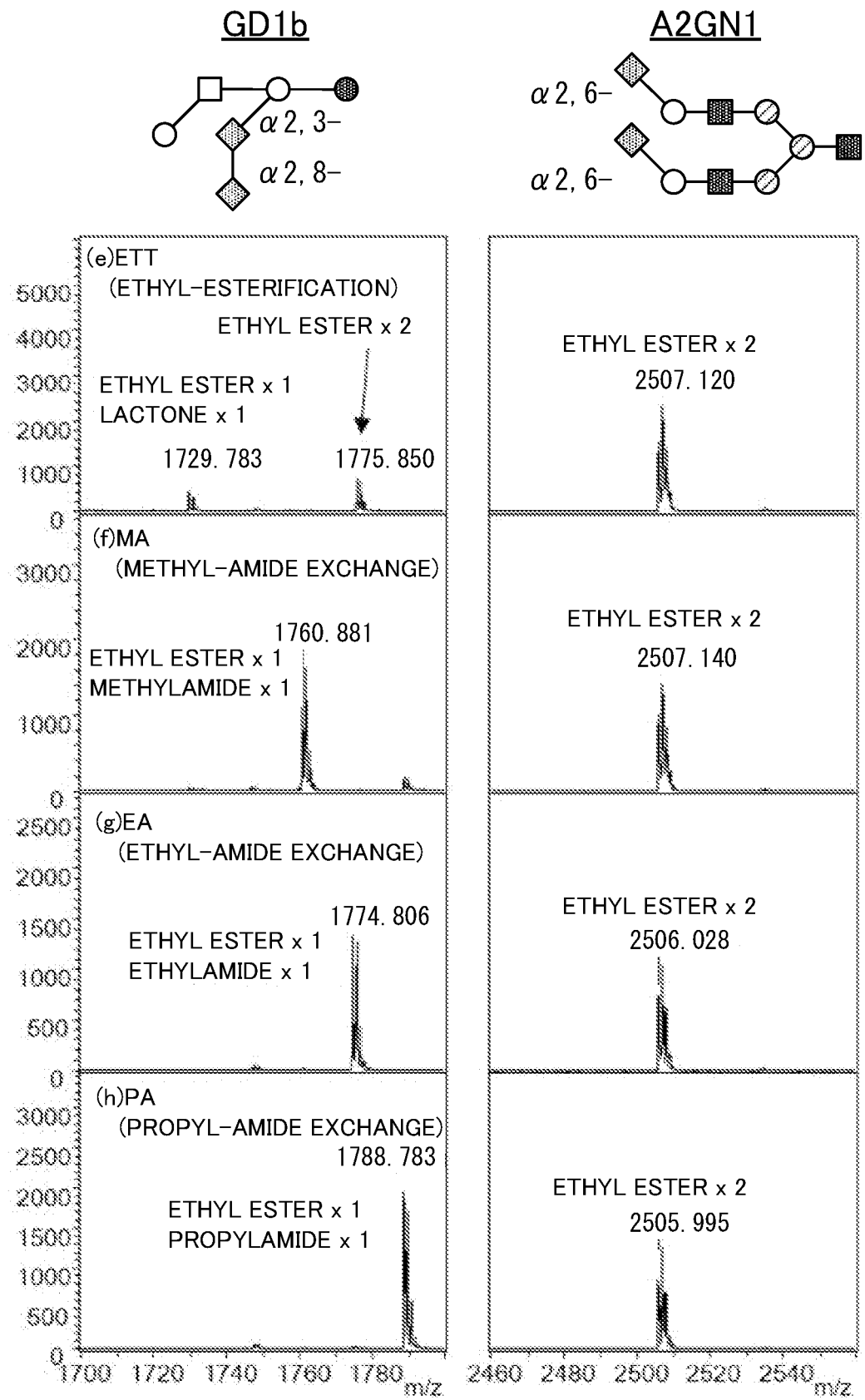
FIG. 17 shows (e) mass spectra of analysis samples prepared in such a manner that, for the glycan GD1b and the glycan A2GN1, ethyl-esterification reaction was performed and amidation reaction was not performed, and mass spectra of analysis samples prepared in such a manner that, for the glycan GD1b and the glycan A2GN1, ethyl-esterification reaction was performed and amidation reaction was then performed by using (f) methylamine solution, (g) ethylamine solution, or (h) propylamine solution with a solvent of acetonitrile.

FIG. 17 shows mass spectra of samples obtained in such a manner that, for the glycans GD1b and A2GN1 for the samples, modification reaction through ethyl-esterification was performed, and (e) amidation reaction was not performed thereafter, or (f, g, h) amidation reaction was then performed with acetonitrile solution containing 1 M (M denotes mol/L) methylamine, ethylamine, or propylamine. For GD1b, when ethyl-esterification with ETT was performed and amidation was not performed, a peak corresponding to the case that one α2,3-sialic acid and one α2,8-sialic acid were methyl-esterified (m/z 1776) was detected. When amidation reaction with methylamine solution was performed after methyl-esterification, products converged to a product in which only one sialic acid was methylamidated (m/z 1761). When ethylamine or propylamine solution was used, similarly, products converged to a product in which only one sialic acid was amidated (m/z 1775, 1789). In all of the reactions relating to (a) to (d) in FIG. 16 and (e) to (h) in FIG. 17, the glycan A2GN1, which includes α2,6-sialic acid and was added as an internal standard glycan, was detected as an ethyl ester form.

Figure 18:
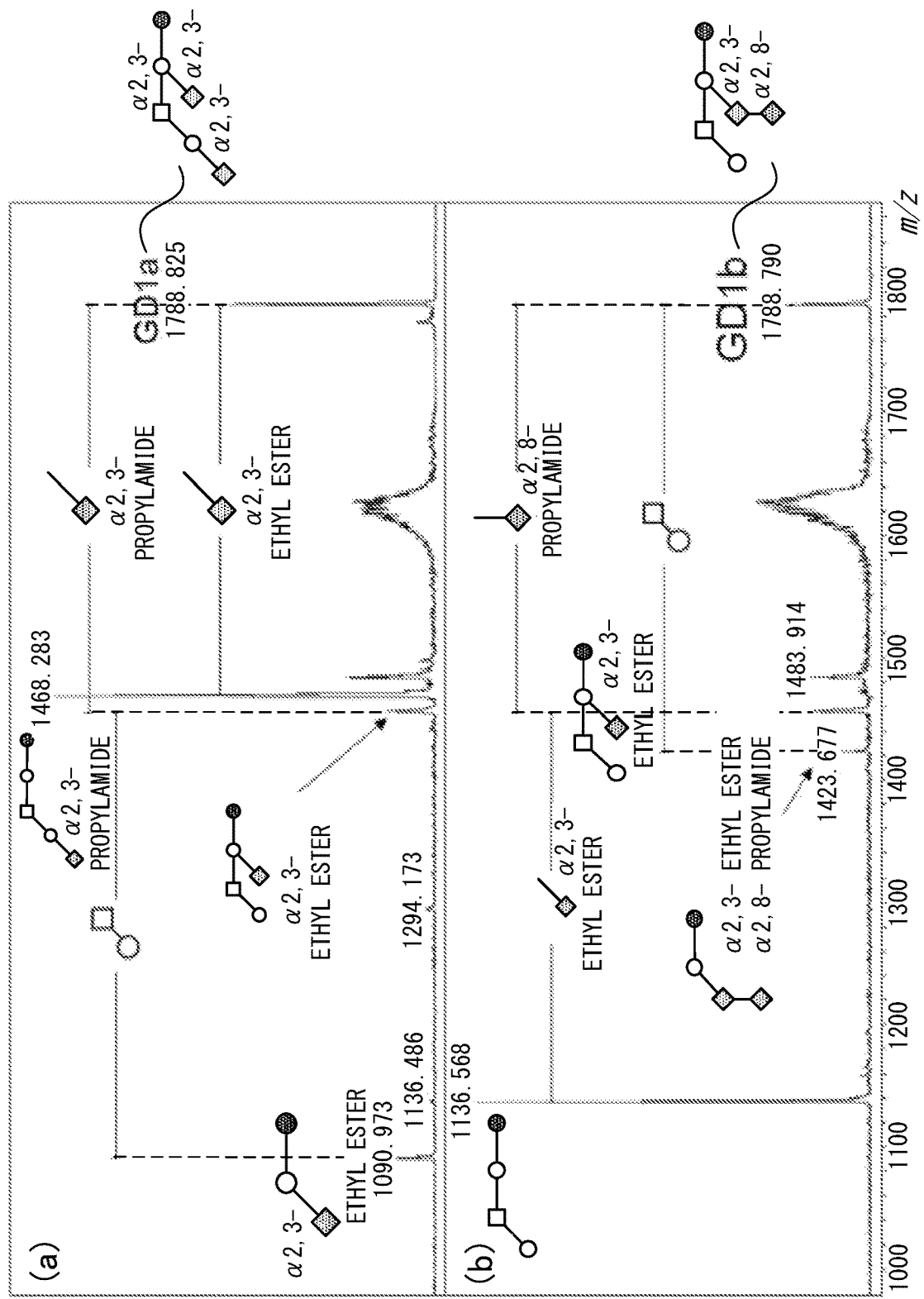
FIG. 18 shows MS/MS spectra of analysis samples prepared in such a manner that, for (a) the glycan GD1a and (b) the glycan GD1b, ethyl-esterification reaction was performed and amidation reaction was then performed by using propylamine solution with a solvent of acetonitrile.

FIG. 18 shows MS/MS spectra of GD1a ((a) in FIG. 18) and GD1b ((b) in FIG. 18) (m/z 1779, for both cases) subjected to ethyl-esterification followed by propylamidation. It is understood that, for GD1a, a fragment corresponding to the glycan GM3, which was ethyl-esterified, was detected at m/z 1090, and that, for GD1b, only α2,8-sialic acid was propylamidated. This indicates that site-specific ester-amide exchange was caused to α2,3-/α2,8-sialic acid under the present conditions, and suggests that the above-described method is effective not only for discrimination of linkage types of sialic acid but also for analysis of bonding positions.

Example 9

In Example 9, propylamine solution with a solvent of acetonitrile was used as an amidation reaction solution, and the propylamine concentration of the propylamine solution was adjusted to different concentrations ranging from 0 M to 3 M. With the other settings being the same as those in Example 8, mass spectrometry was performed for the GSL glycan.

Results

Figure 19:
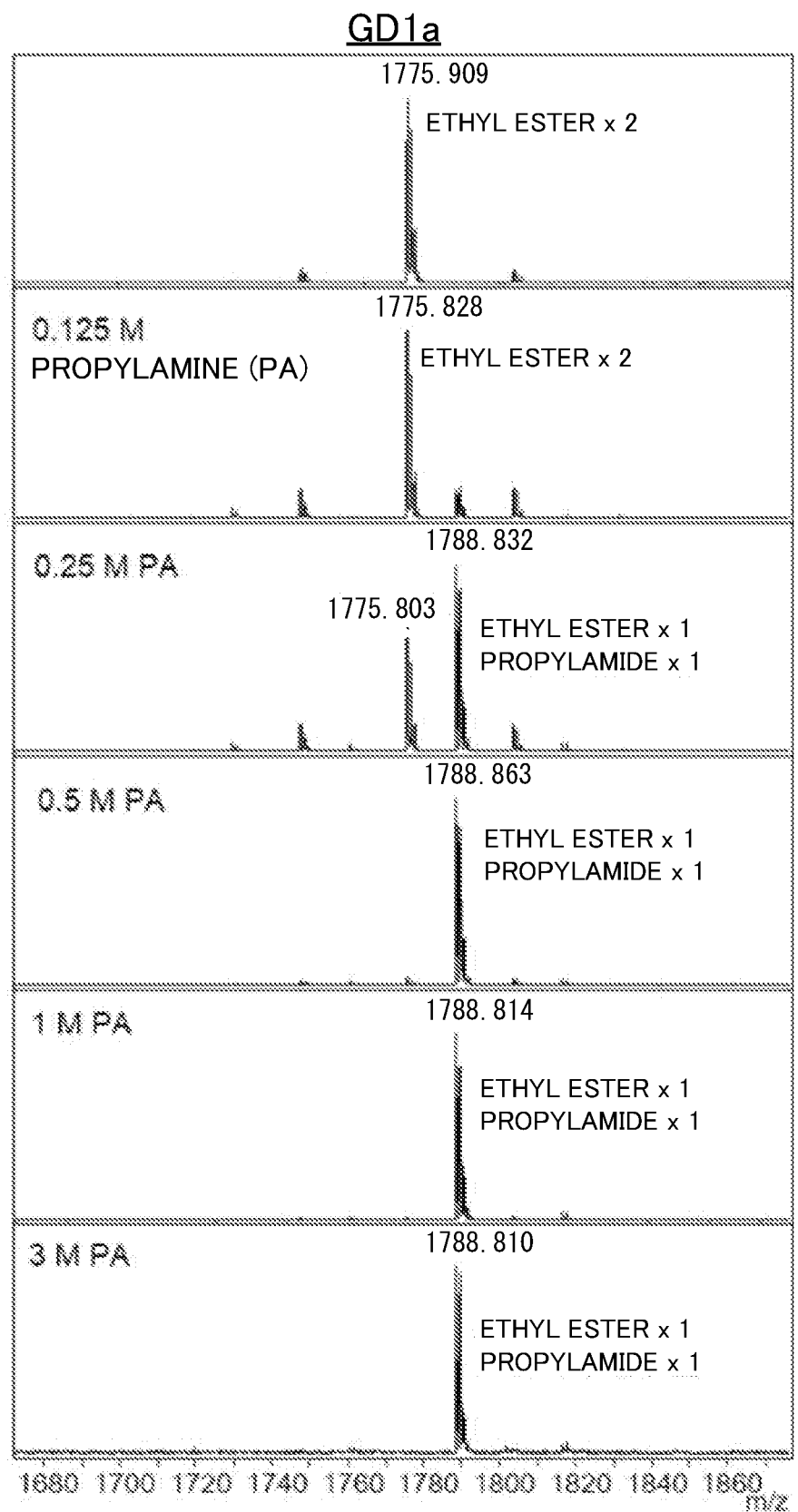
FIG. 19 shows mass spectra of analysis samples prepared in such a manner that, for the glycan GD1a, ethyl-esterification reaction was performed and amidation reaction was performed by using propylamine solution at a concentration of 0 M, 0.125 M, 0.25 M, 0.5 M, 1 M, or 3 M with a solvent of acetonitrile.

FIG. 19 shows mass spectra of GD1a acquired by using different concentrations of the propylamine solution as an amidation reaction solution. For GD1a, ester-amide exchange hardly progressed when 0.125 M propylamine solution was used, and only one α2,3-sialic acid present at the end of the glycan was propylamidated when a concentration of 0.25 M or 0.5 M or higher was used.

Figure 20:
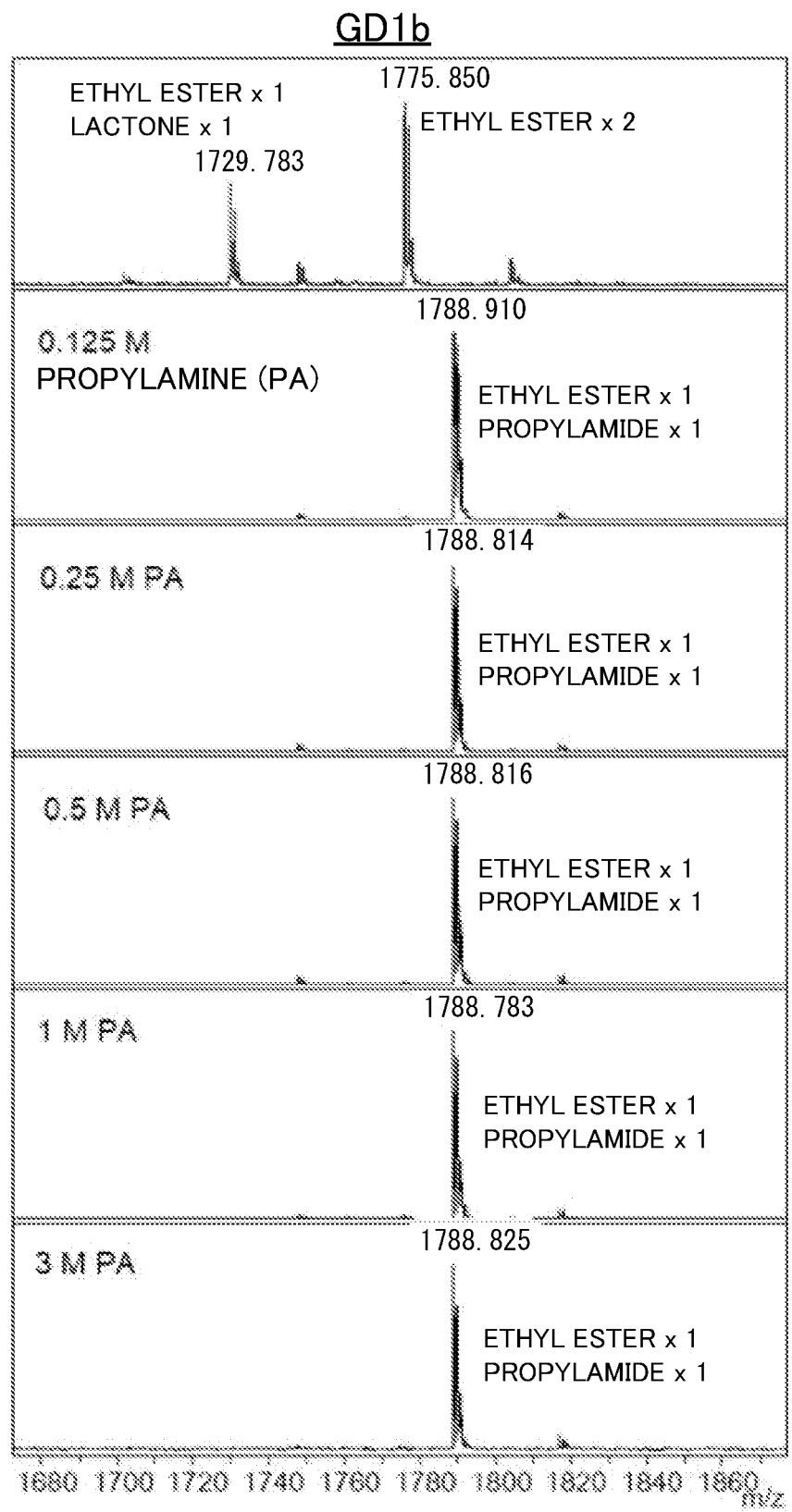
FIG. 20 shows mass spectra of analysis samples prepared in such a manner that, for the glycan GD1b, ethyl-esterification reaction was performed and amidation reaction was then performed by using propylamine solution at a concentration of 0 M, 0.125 M, 0.25 M, 0.5 M, 1 M, or 3 M with a solvent of acetonitrile.

FIG. 20 shows mass spectra of GD1b acquired by using different concentrations of the propylamine solution as an amidation reaction solution. For GD1b, only α2,8-sialic acid, which readily undergoes lactone formation, was propylamidated, without depending on propylamine concentration. The results not only indicate optimum concentrations for amidation of α2,3- or α2,8-sialic acid ester present at the end, but also suggest that α2,8-sialic acid and α2,3-sialic acid can be distinguished from each other.

REFERENCE SIGNS LIST

10: Esterifying agent
11: Container
100: Kit for preparing analysis sample

The invention claimed is:

1. A method for preparing an analysis sample from a sample containing a glycan, the method comprising:
   1) Performing esterification reaction on the sample that subjects at least a part of a sialic acid included in the glycan to esterification other than lactonization; and
   2) Performing amidation reaction that converts an esterified form of the sialic acid modified through the esterification other than lactonization according to step 1 into an amidated form through contacting the at least a part of the sample after the esterification reaction according to step 1 with an amidation reaction solution containing at least one compound selected from the group consisting of ammonia, amines, hydrazine, hydrazine derivatives, and hydroxyamine, and salts thereof to be reacted with the sialic acid modified through the esterification.

2. The method for preparing an analysis sample according to claim 1, comprising:
   performing the esterification reaction through contacting the sample with an esterification reaction solution, wherein
   the esterification reaction solution contains at least one of an alcohol and an esterifying agent.

3. The method for preparing an analysis sample according to claim 2, wherein:
   the esterification reaction solution contains the esterifying agent; and
   the esterifying agent is a triazene derivative.

4. The method for preparing an analysis sample according to claim 2, wherein
   the amidation reaction is performed only through contacting the sample with the amidation reaction solution after an operation to remove the esterification reaction solution from the sample.

5. The method for preparing an analysis sample according to claim 2, wherein
   the amidation reaction solution is free of a dehydration condensation agent.

6. The method for preparing an analysis sample according to claim 2, wherein:
   at least a part of a sialic acid not modified through the esterification is lactonized through contacting the sample with the esterification reaction solution; and
   a lactone structure of the sialic acid modified through the lactonization is converted into an amidated form through contacting the sample with the amidation reaction solution.

7. The method for preparing an analysis sample according to claim 1, wherein
   an operation of reacting the sample with a dehydration condensation agent is not performed after contacting the sample with the amidation reaction solution.

8. The method for preparing an analysis sample according to claim 1, wherein
   a time during which the sample is in contact with the amidation reaction solution to perform the amidation reaction is shorter than 30 minutes.

9. The method for preparing an analysis sample according to claim 1, wherein
   an operation to cleave a lactone structure formed through the esterification reaction is not performed before the amidation reaction.

10. The method for preparing an analysis sample according to claim 1, wherein
    the at least one compound is a primary amine.

11. The method for preparing an analysis sample according to claim 10, wherein
one or no carbon atom is directly bonding to a carbon atom bonding to an amino group of the primary amine.

12. The method for preparing an analysis sample according to claim 1, wherein
the at least one compound includes an alkyl group.

13. The method for preparing an analysis sample according to claim 1, wherein
pH of the amidation reaction solution is 7.7 or higher.

14. The method for preparing an analysis sample according to claim 1, wherein
at least one sialic acid selected from the group consisting of α2,3-sialic acid, α2,8-sialic acid, and α2,9-sialic acid is amidated in the amidation reaction.

15. The method for preparing an analysis sample according to claim 14, wherein
a concentration of the at least one compound in the amidation reaction solution for the amidation reaction is controlled so as not to cause conversion of an esterified form of α2,6-sialic acid modified through the esterification into the amidated form.

16. The method for preparing an analysis sample according to claim 1, wherein
at least one of the esterification reaction and the amidation reaction is performed in such a state that the sample is bonding to or adsorbed on a solid phase carrier.

17. The method for preparing an analysis sample according to claim 1, wherein
a solvent of the amidation reaction solution contains an organic solvent.

18. The method for preparing an analysis sample according to claim 17, wherein
the organic solvent is acetonitrile.

19. The method for preparing an analysis sample according to claim 17, wherein
at least one sialic acid selected from the group consisting of α2,3-sialic acid, α2,8-sialic acid, and α2,9-sialic acid in the amidation reaction is amidated on the basis of a position of the at least one sialic acid in the glycan or a structure of the glycan.

20. The method for preparing an analysis sample according to claim 19, further comprising:
performing the amidation reaction by using an amidation reaction solution containing the organic solvent, and then performing amidation of a sialic acid not amidated through the amidation reaction through contacting an amidation reaction solution containing an aqueous solvent with the sample that has been subjected to the amidation reaction.

21. The method for preparing an analysis sample according to claim 1,
comprising: preparing a first sample from the analysis sample; and
preparing a second sample from the sample after being subjected to the esterification reaction and before being subjected to the amidation reaction.

22. An analysis method comprising:
preparing the first sample and the second sample by using the method for preparing an analysis sample according to claim 21;
performing analysis of the first sample and the second sample prepared; and
performing data analysis of a glycan contained in the sample before the esterification reaction on the basis of a difference between data acquired in the analysis for the first sample and data acquired in the analysis for the second sample.

23. An analysis method comprising:
preparing a sample by using the method for preparing an analysis sample according to claim 1; and
performing analysis of the analysis sample prepared.

24. The analysis method according to claim 23, wherein
the analysis is performed through at least one of mass spectrometry and chromatography.

* * * * *